US007923587B2

(12) United States Patent (10) Patent No.: US 7,923,587 B2
Cholli (45) Date of Patent: Apr. 12, 2011

(54) ANTI-OXIDANT MACROMONOMERS AND POLYMERS AND METHODS OF MAKING AND USING THE SAME

(75) Inventor: Ashok L. Cholli, Chelmsford, MA (US)

(73) Assignee: Polnox Corporation, Lowell, MA (US)

( * ) Notice: Subject to any disclaimer, the term of this patent is extended or adjusted under 35 U.S.C. 154(b) by 0 days.

(21) Appl. No.: 12/154,911

(22) Filed: May 28, 2008

(65) Prior Publication Data

US 2008/0311065 A1 Dec. 18, 2008

Related U.S. Application Data

(63) Continuation of application No. 11/184,724, filed on Jul. 19, 2005, now abandoned.

(60) Provisional application No. 60/590,575, filed on Jul. 23, 2004, provisional application No. 60/590,646, filed on Jul. 23, 2004.

(51) Int. Cl.
*C07C 39/12* (2006.01)
*C06B 23/00* (2006.01)
*C06B 43/00* (2006.01)
*C01B 3/00* (2006.01)
*C01B 6/00* (2006.01)
*C02F 1/70* (2006.01)

(52) U.S. Cl. .................... 568/729; 568/717; 252/188.28
(58) Field of Classification Search .................. 526/313; 528/86; 252/188.28; 568/717, 729
See application file for complete search history.

(56) References Cited

U.S. PATENT DOCUMENTS

| 3,116,305 A | * | 12/1963 | Morris et al. .................... 560/85 |
| 3,294,836 A | * | 12/1966 | Dexter et al. .................... 560/86 |
| 3,441,545 A | * | 4/1969 | Blatz et al. ..................... 525/340 |
| 3,459,704 A | * | 8/1969 | Peterson et al. ............. 524/289 |
| 3,557,245 A | | 1/1971 | Phillips et al. |
| 3,632,785 A | * | 1/1972 | Bornstein ..................... 525/480 |
| 3,645,970 A | * | 2/1972 | Kleiner ......................... 526/313 |
| 3,649,667 A | * | 3/1972 | Song ............................ 560/75 |
| 3,655,831 A | * | 4/1972 | Friedman ....................... 558/78 |
| 3,870,680 A | * | 3/1975 | Schurdak ...................... 524/194 |
| 3,907,939 A | | 9/1975 | Robin et al. |
| 3,953,402 A | * | 4/1976 | Kline ............................ 526/195 |
| 3,965,039 A | | 6/1976 | Chaplits et al. |
| 3,983,091 A | | 9/1976 | Gloth et al. |
| 3,994,828 A | | 11/1976 | Zaffaroni |
| 3,996,160 A | * | 12/1976 | Dale et al. ..................... 252/404 |
| 3,996,198 A | * | 12/1976 | Wang et al. .................... 528/205 |
| 4,054,676 A | * | 10/1977 | Weinshenker et al. ....... 426/546 |
| 4,094,857 A | * | 6/1978 | Wolfe, Jr. ....................... 524/222 |
| 4,096,319 A | * | 6/1978 | Willette et al. ............... 526/257 |
| 4,097,464 A | * | 6/1978 | Kline ............................ 526/313 |
| 4,098,829 A | * | 7/1978 | Weinshenker et al. ....... 568/741 |
| 4,107,144 A | * | 8/1978 | Russell et al. ................. 526/212 |
| 4,136,055 A | * | 1/1979 | Lyons ............................ 252/404 |
| 4,202,816 A | * | 5/1980 | Moser et al. ................... 524/99 |
| 4,205,151 A | * | 5/1980 | Dale et al. ..................... 526/262 |
| 4,213,892 A | * | 7/1980 | Scott ............................. 525/150 |
| 4,219,453 A | * | 8/1980 | Sakurai et al. ................ 524/291 |
| 4,267,358 A | * | 5/1981 | Hechenbleikner et al. ..... 560/75 |
| 4,281,192 A | * | 7/1981 | Jacquet et al. ................ 564/207 |
| 4,283,572 A | * | 8/1981 | Klicker ......................... 568/783 |
| 4,317,933 A | * | 3/1982 | Parker .......................... 568/433 |
| 4,341,879 A | * | 7/1982 | Sugio et al. ..................... 524/91 |
| 4,355,148 A | * | 10/1982 | Layer et al. ................... 526/281 |
| 4,377,666 A | * | 3/1983 | Farrar ........................... 525/132 |
| 4,380,554 A | | 4/1983 | Serres, Jr. |
| 4,447,657 A | * | 5/1984 | Firth et al. .................... 568/783 |
| 4,465,871 A | * | 8/1984 | Firth et al. .................... 568/783 |
| 4,510,296 A | * | 4/1985 | Hergenrother ................ 525/534 |
| 4,511,491 A | * | 4/1985 | Ishii et al. ...................... 252/404 |
| 4,634,728 A | | 1/1987 | Dunski et al. |
| 4,690,995 A | * | 9/1987 | Keskey et al. ................ 526/286 |
| 4,761,247 A | * | 8/1988 | Rei et al. ....................... 252/364 |
| 4,824,929 A | * | 4/1989 | Arimatsu et al. ............. 528/205 |
| 4,849,503 A | * | 7/1989 | Cotter et al. .................. 528/171 |
| 4,855,345 A | * | 8/1989 | Rosenberger et al. ........ 524/120 |
| 4,857,596 A | * | 8/1989 | MacLeay et al. ............. 525/142 |
| 4,870,214 A | * | 9/1989 | Mina et al. .................... 568/720 |
| 4,894,263 A | * | 1/1990 | Dubois et al. ................. 428/1.5 |
| 4,897,438 A | | 1/1990 | Kikuchi et al. |

(Continued)

FOREIGN PATENT DOCUMENTS

CZ 111291 6/1964

(Continued)

OTHER PUBLICATIONS

Al-Malaika et al. Polymer degradation and Stability, 49, 1995, 77-89.* International Search Report for related foreign application PCT/US2007/015177, mailed on Jun. 13, 2008.
Thompson, C. Ray, "Stability of Carotene in Alfalfa Meal: Effect of Antioxidants," *Industrial & Engineering Chemistry*, 24(5): 922-925 (1950).
Dordick, J.S., et al., "Polymerization of Phenols Catalyzed by Peroxidase in Nonaqueous Media," *Biotechnology and Bioengineering*, 30(1):31-36 (1987).
Kazandjian, R.Z., et al., "Enzymatic Analyses in Organic Solvents," *Biotechnology and Bioengineering*, XXVIII:417-421 (1986).
Klibanov, A.M., et al., "Enzymatic Removal of Toxic Phenols and Anilines from Waste Waters," *J. of Applied Biochemistry*, 2(5):414-421 (1980).

(Continued)

*Primary Examiner* — Mark Eashoo
*Assistant Examiner* — Liam J Heincer
(74) *Attorney, Agent, or Firm* — Hamilton, Brook, Smith & Reynolds, P.C.

(57) ABSTRACT

The present invention relates to macromonomer compounds possessing antioxidant properties, antioxidant polymers comprising the antioxidant macromonomers as a recurring unit, and methods of inhibiting oxidation in a substance comprising contacting the substance with the antioxidant polymers. In one embodiment, substantially all of the recurring macromonomeric units of the antioxidant polymers comprise an antioxidant moiety. In another embodiment, all of the recurring macromonomer units of the antioxidant polymers comprise an antioxidant moiety. The method of the present invention, yields antioxidant polymers with substantially all of the recurring units comprising an antioxidant moiety. These antioxidant polymers have greater bulk antioxidative properties than previously known.

2 Claims, 8 Drawing Sheets

U.S. PATENT DOCUMENTS

| | | | | |
|---|---|---|---|---|
| 4,900,671 A * | 2/1990 | Pokora et al. | 435/156 |
| 4,925,591 A | 5/1990 | Nakauchi et al. | |
| 4,968,759 A * | 11/1990 | Kikuchi et al. | 525/534 |
| 4,977,004 A * | 12/1990 | Bettle et al. | 428/36.7 |
| 4,981,917 A * | 1/1991 | MacLeay et al. | 525/348 |
| 4,994,628 A * | 2/1991 | Goddard et al. | 568/720 |
| 5,013,470 A * | 5/1991 | Benfaremo | 508/471 |
| 5,017,727 A * | 5/1991 | Olivier | 568/719 |
| 5,082,358 A * | 1/1992 | Tabata et al. | 359/642 |
| 5,102,962 A | 4/1992 | Kikuchi et al. | |
| 5,117,063 A | 5/1992 | Stern et al. | |
| 5,143,828 A * | 9/1992 | Akkara et al. | 435/41 |
| 5,155,153 A | 10/1992 | Neri et al. | |
| 5,185,391 A * | 2/1993 | Stokich, Jr. | 524/87 |
| 5,185,407 A * | 2/1993 | Wong | 525/328.8 |
| 5,188,953 A * | 2/1993 | Johnson et al. | 435/156 |
| 5,191,008 A * | 3/1993 | Frost et al. | 524/460 |
| 5,196,142 A * | 3/1993 | Mollet et al. | 516/75 |
| 5,206,303 A * | 4/1993 | Tse et al. | 525/319 |
| 5,207,939 A * | 5/1993 | Farng et al. | 508/557 |
| 5,274,060 A * | 12/1993 | Schadeli | 526/270 |
| 5,278,055 A | 1/1994 | Cyrus, Jr. et al. | |
| 5,304,589 A | 4/1994 | Davidson et al. | |
| 5,320,889 A * | 6/1994 | Bettle, III | 428/36.6 |
| 5,449,715 A * | 9/1995 | Plochocka et al. | 524/556 |
| 5,498,809 A | 3/1996 | Emert et al. | |
| RE35,247 E | 5/1996 | Cyrus, Jr. et al. | |
| 5,516,856 A * | 5/1996 | Sanchez | 525/447 |
| 5,541,091 A * | 7/1996 | Wheeler et al. | 435/128 |
| 5,565,300 A * | 10/1996 | Uenishi et al. | 430/192 |
| 5,574,118 A * | 11/1996 | Olivier | 526/281 |
| 5,652,201 A | 7/1997 | Papay et al. | |
| 5,739,341 A * | 4/1998 | Dubs et al. | 546/217 |
| 5,834,544 A * | 11/1998 | Lin et al. | 524/217 |
| 5,837,798 A | 11/1998 | Hutchings et al. | |
| 5,869,592 A * | 2/1999 | Gagne et al. | 528/8 |
| 5,911,937 A * | 6/1999 | Hekal | 264/255 |
| 5,994,498 A * | 11/1999 | Tripathy et al. | 528/422 |
| 6,018,018 A * | 1/2000 | Samuelson et al. | 528/422 |
| 6,046,284 A * | 4/2000 | Rasberger et al. | 524/244 |
| 6,096,695 A * | 8/2000 | Lam et al. | 508/570 |
| 6,096,859 A * | 8/2000 | Akkara et al. | 528/501 |
| 6,150,491 A * | 11/2000 | Akkara | 528/86 |
| 6,232,314 B1 * | 5/2001 | Jarrott et al. | 514/252.12 |
| 6,342,549 B1 * | 1/2002 | Hirose et al. | 524/120 |
| 6,444,450 B2 * | 9/2002 | Akkara et al. | 435/108 |
| 6,646,035 B2 * | 11/2003 | Koch et al. | 524/291 |
| 6,723,815 B2 * | 4/2004 | Callaghan et al. | 526/303.1 |
| 6,743,525 B2 * | 6/2004 | Berntsen et al. | 428/690 |
| 6,770,785 B1 * | 8/2004 | Desai et al. | 564/355 |
| 6,794,480 B2 * | 9/2004 | Goto et al. | 528/125 |
| 6,800,228 B1 * | 10/2004 | Semen | 264/109 |
| 6,828,364 B2 * | 12/2004 | Gugumus | 524/95 |
| 7,132,496 B2 | 11/2006 | Kerres et al. | |
| 7,169,844 B2 * | 1/2007 | Inokami | 524/591 |
| 7,205,350 B2 * | 4/2007 | Thibaut | 524/291 |
| 7,223,432 B2 * | 5/2007 | Cholli et al. | 426/541 |
| 7,262,319 B2 * | 8/2007 | Rehm et al. | 560/75 |
| 7,705,176 B2 | 4/2010 | Cholli et al. | |
| 2001/0041203 A1* | 11/2001 | Uno et al. | 426/488 |
| 2002/0007020 A1* | 1/2002 | Higashimura et al. | 525/390 |
| 2002/0128493 A1* | 9/2002 | Romanczyk et al. | 549/399 |
| 2002/0143025 A1* | 10/2002 | Pratt et al. | 514/269 |
| 2002/0183470 A1* | 12/2002 | Tripathy et al. | 526/217 |
| 2003/0030033 A1* | 2/2003 | Duyck et al. | 252/380 |
| 2003/0078346 A1* | 4/2003 | Nakamura et al. | 525/329.7 |
| 2003/0091837 A1* | 5/2003 | Aoki | 428/447 |
| 2003/0176620 A1 | 9/2003 | Romanczyk, Jr. et al. | |
| 2003/0191242 A1* | 10/2003 | Zedda et al. | 525/92 L |
| 2003/0229196 A1* | 12/2003 | Braat et al. | 528/86 |
| 2003/0230743 A1 | 12/2003 | Cholli et al. | |
| 2004/0015021 A1* | 1/2004 | Adams et al. | 568/798 |
| 2004/0164279 A1* | 8/2004 | Stevenson et al. | 252/397 |
| 2004/0180994 A1 | 9/2004 | Pearson et al. | |
| 2004/0186167 A1* | 9/2004 | Dou et al. | 514/456 |
| 2004/0186214 A1 | 9/2004 | Li et al. | |
| 2004/0198875 A1 | 10/2004 | Kaprinidis et al. | |
| 2004/0214935 A1* | 10/2004 | Cholli et al. | 524/342 |
| 2005/0170978 A1* | 8/2005 | Migdal et al. | 508/497 |
| 2005/0209379 A1 | 9/2005 | Botkin et al. | |
| 2005/0238789 A1* | 10/2005 | Cholli et al. | 426/654 |
| 2005/0242328 A1* | 11/2005 | Baranski | 252/397 |
| 2006/0029706 A1* | 2/2006 | Cholli et al. | 426/541 |
| 2006/0040833 A1 | 2/2006 | Al-Akhdar et al. | |
| 2006/0041087 A1* | 2/2006 | Cholli | 526/89 |
| 2006/0041094 A1* | 2/2006 | Cholli | 526/313 |
| 2006/0128929 A1* | 6/2006 | Yang et al. | 528/86 |
| 2006/0128930 A1* | 6/2006 | Dhawan et al. | 528/86 |
| 2006/0128931 A1* | 6/2006 | Kumar et al. | 528/183 |
| 2006/0128939 A1* | 6/2006 | Kumar et al. | 528/373 |
| 2006/0154818 A1* | 7/2006 | Destro et al. | 503/201 |
| 2006/0189820 A1* | 8/2006 | Rehm et al. | 560/67 |
| 2006/0189824 A1* | 8/2006 | Kumar et al. | 562/442 |
| 2006/0208227 A1* | 9/2006 | Shiraki | 252/401 |
| 2006/0233741 A1* | 10/2006 | Kumar et al. | 424/78.27 |
| 2007/0010632 A1* | 1/2007 | Kaplan et al. | 525/423 |
| 2007/0106059 A1* | 5/2007 | Cholli et al. | 528/422 |
| 2007/0135539 A1* | 6/2007 | Cholli et al. | 524/120 |
| 2007/0149660 A1* | 6/2007 | Kumar et al. | 524/115 |
| 2007/0154430 A1 | 7/2007 | Cholli et al. | |
| 2007/0154608 A1* | 7/2007 | Cholli et al. | 426/541 |
| 2007/0154720 A1* | 7/2007 | Cholli et al. | 428/411.1 |
| 2007/0161522 A1* | 7/2007 | Cholli et al. | 508/545 |
| 2008/0249335 A1 | 10/2008 | Cholli et al. | |
| 2008/0293856 A1 | 11/2008 | Kumar et al. | |
| 2008/0311065 A1 | 12/2008 | Cholli | |
| 2009/0184294 A1 | 7/2009 | Cholli et al. | |

FOREIGN PATENT DOCUMENTS

| | | |
|---|---|---|
| DE | 197 47 644 A1 | 5/1999 |
| DE | 198 43 875 A1 | 3/2000 |
| EP | 0 181 023 A1 | 5/1986 |
| EP | 0 289 077 A2 | 11/1988 |
| EP | 0 358 157 | 3/1990 |
| EP | 0 404 039 A1 | 12/1990 |
| EP | 0 618 203 A1 | 10/1994 |
| EP | 0 688 805 A1 | 12/1995 |
| EP | 1 067 144 A1 | 1/2001 |
| EP | 1 468 968 A1 | 10/2004 |
| FR | 2 183 973 | 12/1973 |
| GB | 1 283 103 | 7/1972 |
| GB | 1 320 169 | 6/1973 |
| GB | 1 372 042 | 10/1974 |
| GB | 1 389 442 | 4/1975 |
| GB | 1 469 245 | 4/1977 |
| GB | 1 482 649 | 8/1977 |
| JP | 69002715 B | 1/1966 |
| JP | 43016392 B4 | 7/1968 |
| JP | 44024274 | 10/1969 |
| JP | 44028850 | 11/1969 |
| JP | 45 2980 | 1/1970 |
| JP | 49 29339 | 3/1974 |
| JP | 57085366 A | 5/1982 |
| JP | 59025814 | 2/1984 |
| JP | 59197447 | 11/1984 |
| JP | 60-199832 | 10/1985 |
| JP | 05 199858 | 8/1993 |
| JP | 06135876 A | 5/1994 |
| JP | 06 247959 | 9/1994 |
| JP | 08027226 A | 1/1996 |
| JP | 09262069 | 10/1997 |
| JP | 09 328519 | 12/1997 |
| JP | 09 328521 | 12/1997 |
| JP | 9322784 A | 12/1997 |
| JP | 11-80063 | 3/1999 |
| JP | 11-158103 | 6/1999 |
| JP | 2003138258 | 5/2003 |
| NL | 7 905 000 | 3/1980 |
| WO | WO 92/20734 | 11/1992 |
| WO | WO 00/39064 | 7/2000 |
| WO | WO 01/18125 A1 | 3/2001 |
| WO | WO 01/48057 A1 | 7/2001 |
| WO | WO 02/079130 A1 | 10/2002 |
| WO | WO 03/087260 A1 | 10/2003 |
| WO | WO 03/102004 A1 | 12/2003 |
| WO | WO 2004/024070 A2 | 3/2004 |
| WO | WO 2004/050795 A2 | 6/2004 |

| | | |
|---|---|---|
| WO | WO 2005/025513 A2 | 3/2005 |
| WO | WO 2005/025646 A2 | 3/2005 |
| WO | WO 2005/060500 A2 | 7/2005 |
| WO | WO 2005/070974 A2 | 8/2005 |
| WO | WO 2005/071005 A1 | 8/2005 |
| WO | WO 2006/018403 A1 | 2/2006 |
| WO | WO 2006/060801 A2 | 6/2006 |
| WO | WO 2006/104957 A2 | 10/2006 |
| WO | WO 2008/005358 A2 | 1/2008 |

OTHER PUBLICATIONS

Ikeda, R., et al., "Novel Synthetic Pathway to a Poly(phenylene oxide). Laccase-Catalyzed Oxidative Polymerization of Syringic Acid," *Macromolecules*, 29:3053-3054 (1996).

Akkara, J.A., et al., "Synthesis and Characterization of Polymers Produced by Horseradish Peroxidase in Dioxane," *J. of Polymer Science: Part A: Polymer Chemistry*, 29(11):1561-1574 (1991).

Ayyagari, M.S., et al., "Controlled Free-Radical Polymerization of Phenol Derivatives by Enzyme-Catalyzed Reactions in Organic Solvents," *Macromolecules*, 28(15):5192-5197 (1995).

Ryu, K., et al., "Peroxidase-Catalyzed Polymerization of Phenols," Biocatalysis in Agricultural Biotechnology, Chapter10:141-157 (1988).

Bruno, F.F., et al., "Enzymatic Template Synthesis of Polyphenol," Materials Research Society Symposium Proceedings vol. 600, Electroactive Polymers (EAP):255-259 (1999).

Akkara, J.A., et al., "Hematin-Catalyzed Polymerization of Phenol Compounds," Macromolecules, 33(7):2377-2382 (2000).

Dordick, J.S., "Enzymatic Catalysis in Monophasic Organic Dolvents," *Enzyme Microb. Technol.*, 11(4):194-211 (1989).

FS&T 821 "Food Lipids," [online], Oct. 2001 [retrieved on Oct. 29, 2002]. Retrieved from the Internet <URL: http://class.fst.ohio-state.edu/fst821/>.

FST 821 "Course Schedule," [online], [retrieved on Oct. 29, 2002]. Retrieved from the Internet <URL: http://class.fst.ohio-state.edu/fst821/>.

FS&T 821 "Antioxidant," [online], [retrieved on Oct. 29, 2002]. Retrieved from the Internet <URL: http://class.fst.ohio-state.edu/fst821/>.

Jialanella, G.and Pilrma, I.,"Synthesis of Poly(vinyl alcohol-co-vinyl gallate) by the Chemical Modification of Poly(vinyl alcohol)," Polymer Bulletin 18:385-389 (1987).

Jayaprakasha, G.K., et al.,"Antioxidant Activity of Grape Seed (*Vitis vinifera*) Extracts on Peroxidation Models In Vitro," *Food Chemistry*, 73:285-290 (2001).

Hidalgo, M.E., et al., "Antioxidant Activity of Depsides and Depsidones," Phytochemistry, 37(6):1585-1587 (1994).

Khan, K.M., et al., "An Expedient Esterification of Aromatic Carboxylic Acids Using Sodium Bromate and Sodium Hydrogen Sulfite," *Tetrahedron* 59(29):5549-5554 (2003).

March, J., Advanced Organic Chemistry, McGraw Hill Book Company, New York, pp. 251-259 (1977).

Mehdipour-Ataei, S., et al., "Novel Diols Containing Ester and Amide Groups and Resulting Poly(ester amide ester)s," *J. Applied Polymer Sci.*, 93:2699-2703 (2004), XP002420014.

Database Beilstein [online] Beilstein Institut Zur Förderung Der Chemischen Wissenschaften; XP002420027, Beilstein Registry No. 3517906.

Database Beilstein [online] Beilstein Institut Zur Förderung Der Chemischen Wissenschaften; XP002420028, Beilstein Registry No. 5840042.

Database Beilstein [online] Beilstein Institut Zur Förderung Der Chemischen Wissenschaften; XP002420029, Beilstein Registry No. 2311871.

Database Beilstein [online] Beilstein Institut Zur Förderung Der Chemischen Wissenschaften; XP002420030, Beilstein Registry No. 8876646.

Database Beilstein [online] Beilstein Institut Zur Förderung Der Chemischen Wissenschaften; XP002420031, Beilstein Registry No. 2271400.

Database Beilstein [online] Beilstein Institut Zur Förderung Der Chemischen Wissenschaften; XP002420032, Beilstein Registry No. 2212095.

Database Beilstein [online] Beilstein Institut Zur Förderung Der Chemischen Wissenschaften; XP002420033, Beilstein Registry No. 8941955.

Database Beilstein [online] Beilstein Institut Zur Förderung Der Chemischen Wissenschaften; XP002420034, Database Accession No. 2312425.

Database Beilstein [online] Beilstein Institut Zur Förderung Der Chemischen Wissenschaften; XP002420035, Beilstein Registry No. 905950.

Database Beilstein [online] Beilstein Institut Zur Förderung Der Chemischen Wissenschaften; XP002420036, Beilstein Registry No. 2140308.

Database Beilstein [online] Beilstein Institut Zur Förderung Der Chemischen Wissenschaften; XP002420037, Beilstein Registry No. 134886.

Database Beilstein [online] Beilstein Institut Zur Förderung Der Chemischen Wissenschaften; XP002420038, Beilstein Registry No. 1961007.

Database Caplus [online] Chemical Abstracts Service, Columbus, Ohio, US, XP-002387095, Database Accession No. 1981:572206, Effectiveness of Inhibitors in the Oxidation of Jet Fuel with an Initiator, abstract, Kovalev, et al.

Masada, H. and Oishi, Y., "A New Synthesis of aryl *t*-butyl Ethers," *Chem. Letters*, 57-58 (1978).

Ol'dekop, Yu. A., et al. "Simple Synthesis of the tert-butyl Ether of Phenol" Inst. Fiz-Org. Khim., Minsk, USSR. *Zhurnal Obshchei Khimii*, 50(2):475-6 (1980).

Masada, II., et al., "A New Method for the Williamson Ether Synthesis Using *t*-alkyl Halides in Nonpolar Solvents," *The Chemical Society of Japan*, 2:164-166 (1995).

Masada, H. et al., "A New Heterogeneous Williamson Synthesis of Ethers Using *t*-alkyl Substrates," *The Chemical Society of Japan* 3:275-282 (1996).

Tsvetkov, O.N., et al., "Alkylation of Phenols with Higher Olefins. Part I," *Int. Chem. Eng.* 7(1):104-121 (1967).

Sartori G., et al,, "Highly Selective Mono-*tert*-butylation of Aromatic Compounds," *Chem. Ind.*, (London), (22):762-763 (1985).

Koshchii, V.A., et al. "Alkylation of Phenol by Alcohols in the Presence of Alumium Phenolate," *Org. Chem.* 24(7):1358-1361 (1988).

Chandra, K.G. and Sharma, M.M., "Alkylation of Phenol with MTBE and Other tert-butylethers:Cation Exchange Resins as Catalysts," *Catal. Lett.* 19(4):309-317 (1993).

Sakthivel, A., et al., "Vapour Phase Tertiary Butylation of Phenol Over Sulfated Zirconia Catalyst," *Catal. Lett.*, 72(3-4):225-228 (2001).

Quaschning, V., et al., "Properties of Modified Zirconia Used as Friedel-Crafts-Acylation Catalysts," *J. Catal.* 177:164-174 (1998).

Badamali, S.K., et al., "Influence of Aluminium Sources on the Synthesis and Catalytic Activity of Mesoporous AIMCM-41 Molecular Sieves," *Catal. Today* 63:291-295 (2000).

Heidekum, A., et al., "Nafion/Silica Composite Material Reveals High Catalytic Potential in Acylation Reactions," *J. Catal.* 188:230-232 (1999).

Kamitori, Y., et al., "Silica Gel as an Effective Catalyst for the Alkylation of Phenols and Some Heterocylic Aromatic Compounds," *J. Org. Chem.* 49: 4161-4165 (1984).

Armengol, E., et al., "Acid Zeolites as Catalysts in Organic Reactions, *tert*-Butylation of Anthracene, Naphthalene and Thianthrene," *Appl. Catal. A* 149:411-423 (1997).

Lalancette, J.M., et al.,, "Metals Intercalated in Graphite. II. The Friedel-Crafts Reactions with ALCL$_3$-Graphite," *Can. J. Chem.* 52:589-591 (1974).

Overgaag, M., et al., "Rearrangement of Alkyl Phenyl Ethers Over Dealuminated HY Zeolites Under Liquid-Phase Conditions," *Applied Catalysis A: General, Elsevier Sci.*,175(1-2):139-146 (1998).

Devassy, B.M., et al., "Zirconia Supported Phosphotungstic Acid as an Efficient Catalyst for Resorcinol *tert*-Butylation and *n*-Heptane Hydroisomerization," *J. Mol. Catalysis A: Chemical* 221:113-119 (2004).

XP-002419239, "Discover Our World of Effects for Polyolefins," *Ciba Speciality Chemicals*, (2003).

Pirozhenko, V.V., et al., "NMR Study of Topomerization of N-Aroyl-p-Benzoquinonemonoimines," *Russian J. of Organic Chem.*, 31(11):1514-1519 (1995).

Coppinger, G.B., et al., "Photo-Fries Rearrangement of Aromatic Esters. Role of Steric and Electronic Factors" *J. of Phy. Chem.*, 70(11):3479-3489 (1966).

Spano, R., et al., "Substituted Anilides of 3-Monoethyl Ester of 4 Hydroxyisophthalic Acid," *J. of Med. Chem.*, 15(5):552-553 (1972).

Mejias, L., et al. "New Polymers From Natural Phenols Using Horseradish or Soybean Peroxidase," *Macromol. Biosci.*, 2:24-32 (2002).

Ismail, M.N. and Wazzan, A.A., "Evaluation of New Thermal Stabilizers and Antifatigue Agents for Rubber Vulcanizates," *Polymer-Plastics Tech. and Eng.*, 45:751-758 (2006).

Joossens, J., et al., "Diphenyl Phosphonate Inhibitors for the Urokinase-Type Plasminogen Activator: Optimization of the P4 Position," *J. Med. Chem.*, 49:5785-5793 (2006).

Belyaev, A., et al., "Structure-Activity Relationship of Diaryl Phosphonate Esters as Potent Irreversible Dipeptidyl Peptidase IV Inhibitors," *J. Med. Chem.*, 42(6):1041-1052 (1998).

Blokhin, Y.I, et al., "Phosphorylation of Dihydric Phenols with Amides of Phosphorous Acid," *Russian Chem. Bulletin*, 45(9):2250-2251 (1996).

Pätoprstý, V., et al., "$^{13}$C NMR Study of 3,9-Di(alkylphenoxy)-2,4,8,10-tetraoxa-3,9-diphosphaspiro[5.5]undecanes," *Magnetic Resonance in Chem*, 23(2):122-126 (1985).

Singh, A. and Kaplan, D. L., "Biocatalytic Route to Ascorbic Acid-Modified Polymers for Free-Radical Scavenging," *Adv. Matter.*, 15(15):1291-1294 (2003).

Kim, T. H., et al., "Melt Free-Radical Grafting of Hindered Phenol Antioxidant onto Polyethylene," *J. Applied Polymer Science*, 77:2968-2973 (2000).

Faber, K., "Biotransformations in Organic Chemistry," A Textbook, Fourth Completely Revised and Extended Edition, Springer-Verlag pp. 347-349 (1953).

Search Report in international application PCT/US2006/042251 (Feb. 2007).

English Abstract of Kovalev, G. I., et al., "Study of the Effectiveness of Inhibitors in Oxidation of Jet Fuel in a Closed Volume," *Deposited Doc.*, VINITI: 443-82 (1981).

English Abstract of Kovalev, G.I., et al., "Effectiveness of Inhibitors in the Oxidation of Jet Fuel With an Initiator," *J. Neftekhimiya (Petroleum Chemistry)*, 21(2): 287-298 (1981).

Hatayama, K., et al., "Anti-ulcer Effect of Isoprenyl Flavonoids. III.[1]) Synthesis and Anti-ulcer Activity of Metabolites of 2'-Carboxymethoxly-4,4'-bis(3-methyl-2-butenyloxy)chalcone[2])," *Chemical & Pharmaceutical Bulletin*, 33(4), 1327-1333(Apr. 1985).

Scharpe, S.L., et al., "Serine Peptidase Modulators, Their Preparation, and Their Therapeutic Use," Chemical Abstracts Service, ZCAPLUS, document No. 131:223514 (1999).

Maki, M., et al., "Weather-Resistant Colored Polypropylene," Chemical Abstracts Service, ZCAPLUS, document No. 89:111364 (1978).

Ding, et al., "Chemical Trapping Experiments Support a Cation-Radical Mechanism for the Oxidative Polymerization of Aniline," Journal of Polymer Science, Part A: Polymer Chemistry, vol. 37: 2569-2579 (1999).

Circ-Marjanovic, et al., Chemical Oxidative Polymerization of Aminodiphenylamines, Journal of Physical Chemistry B, 112, 23: 6976-6987 (2008).

Li, et al., "Novel Multifunctional Polymers from Aromatic Diamines by Oxidative Polymerizations," Chemical Reviews, vol. 102(9): pp. 2925-2943 (2002).

Hofer, K., et al., "[[(Anilinooxalyl)amino]phenyl] Phosphite Stabilizers for Polypropylene," Chemical Abstracts Service, ZCAPLUS, document No. 77:62780 (1972).

Database CA [online] Chemical Abstracts Service, Columbus, Ohio, US, XP-002429584, Database Accession No. 81::153647, Organic Phosphate Stabilizers for Polyamides and Polyurethanes, abstract, Minagawa, M. (1974).

Translation of Nakatsuka et al. (JP 45-2980), Schreiber Translation, Inc., Jul. 2009.

International Search Report for related foreign application PCT/US2005/044021, mailed on May 22, 2006.

International Search Report for related foreign application PCT/US2005/044022, mailed on May 2, 2006.

International Search Report for related foreign application PCT/US2005/044023, mailed on Nov. 3, 2006.

International Search Report for related foreign application PCT/US2005/044019, mailed on Apr. 28, 2006.

International Search Report for related foreign application PCT/US2005/025646, mailed on Mar. 13, 2006.

International Search Report for related foreign application PCT/US2005/025513, mailed on Mar. 13, 2006.

International Search Report for related foreign application PCT/US2006/006355, mailed on Jul. 31, 2006.

International Search Report for related foreign application PCT/US2006/010985, mailed on Dec. 19, 2006.

International Search Report for related foreign application PCT/US2006/042240, mailed on May 3, 2007.

International Search Report for related foreign application PCT/US2006/042235, mailed on Apr. 27, 2007.

International Search Report for related foreign application PCT/US2006/045929, mailed on Apr. 20, 2007.

Notification of Transmittal of the International Search Report and the Written Opinion of the International Searching Authority, or the Declaration for related foreign application PCT/US2007/015177, mailed on Jun. 13, 2008.

Notification Concerning Transmittal of International Preliminary Report on Patentability for related foreign application PCT/US2007/015177, mailed on Jan. 15, 2009.

Written Opinion for related foreign application PCT/US2005/025646, mailed on Nov. 14, 2006.

Notification Concerning Transmittal of International Preliminary Report on Patentability for related foreign application PCT/US2005/025646, mailed on Dec. 20, 2006.

Office Action for related foreign application EP05773305.7 dated Apr. 24, 2008.

Examiner's Report No. 1 for related foreign application AU 2005269754 dated Apr. 1, 2008.

Examiner's Report No. 1 for related foreign application AU 2005269780 dated Apr. 2, 2008.

Examiner's Report No. 2 for related foreign application AU 2005269754 dated Jan. 5, 2010.

Examiner's Report No. 3 for related foreign application AU 2005269754 dated Jan. 12, 2010.

Notification Concerning Transmittal of International Preliminary Report on Patentability and Written Opinion of the International Searching Authority for related foreign application PCT/US2005/025513, mailed on Feb. 1, 2007.

Office Action for related foreign application EP06720996.5-2103 dated Mar. 23, 2009.

Office Action for related foreign application EP06720996.5-2103 dated Apr. 21, 2008.

RN 85650-63-1, 1984.

Notification Concerning Transmittal of International Preliminary Report on Patentability for related foreign application PCT/US2005/001946, mailed on Aug. 3, 2006.

Notification Concerning Transmittal of International Preliminary Report on Patentability for application PCT/US2006/042251, mailed on May 8, 2008.

Notification Concerning Transmittal of International Search Report and Written Opinion of the International Searching Authority, or the Declaration for application PCT/US2006/042251, mailed on Feb. 22, 2007.

Al-Malaika, S and Suharty, N., "Reactive Processing of Polymers: Mechanisms of Grafting Reactions of Functional Antioxidants on Polyolefins in the Presence of a Coagent," Polymer Degradation and Stability 49: 77-89 (1995).

* cited by examiner

ANTI-OXIDANT MACROMONOMERS AND POLYMERS AND METHODS OF MAKING AND USING THE SAME

RELATED APPLICATIONS

This application is a continuation application of U.S. application Ser. No. 11/184,724, filed on Jul. 19, 2005, now abandoned which claims the benefit of U.S. Application No. 60/590,575, filed on Jul. 23, 2004 and U.S. Application No. 60/590,646, filed on Jul. 23, 2004. The entire teachings of the above applications are incorporated herein by reference.

BACKGROUND OF THE INVENTION

Most organic materials such as plastics, foods, elastomers, fuels, oils, gasoline and lubricants, fibers are susceptible to degradation due to thermal oxidative processes. Harmful, reactive and unstable free radicals are formed during the oxidation process and attack the nearby stable molecules (polymer chains or small molecules) of the materials, "stealing" their electron. The 'attacked' molecule loses its electron, resulting itself a free reactive radical to initiate a cascade of chain reactions. Deterioration of their molecular structures as a result of oxidation processes would affect their shelf life, physical and chemical properties. These oxidative reactions are further enhanced at elevated temperatures. The antioxidant molecules are normally added to protect materials against such destructive effects of harmful and reactive free radicals; These antioxidants neutralize these reactive free radicals by donating one of their electrons to stabilize "reactive" free radicals thus stopping the electron 'stealing' mechanism.

In many of today's commercial and industrial applications it is desirable to have antioxidants that possess (a) enhanced antioxidant properties, and (b) active and thermally stable at elevated temperatures. Designing of new antioxidants possessing these two desired properties is essential today for the following reasons: The amount of synthetic antioxidant added to some materials, especially in processed food products, is restricted and need to follow Food and Drug Administration (FDA) regulations (for example, 21 CFR 110, 115, 185, 515 and 615, 21 CFR 182.1660, 3169 and 3173, and 21 CFR. 184.1660). In most cases the usage is limited to 0.02% by weight in fat or oil portion of food because some antioxidants such as BHA (butylated hydroxy anisole) and BHT (butylated hydroxy toluene) are suspected to be carcinogenic beyond certain concentration. It is desirable to design new antioxidants possessing enhanced antioxidant activities so that the materials are protected with lower amount of synthetic antioxidants. In the case of other applications, thermally stable antioxidants are required to protect the materials at high temperatures. For instance, many polyolefins and thermoplastics are processed at elevated temperatures. At these elevated temperatures, some of the antioxidants used today are themselves prone to degradation at these elevated temperatures. There is a need for antioxidants that are stable and active at elevated temperatures so that the new antioxidants could be used in high temperature material applications.

SUMMARY OF THE INVENTION

Figure 1A:
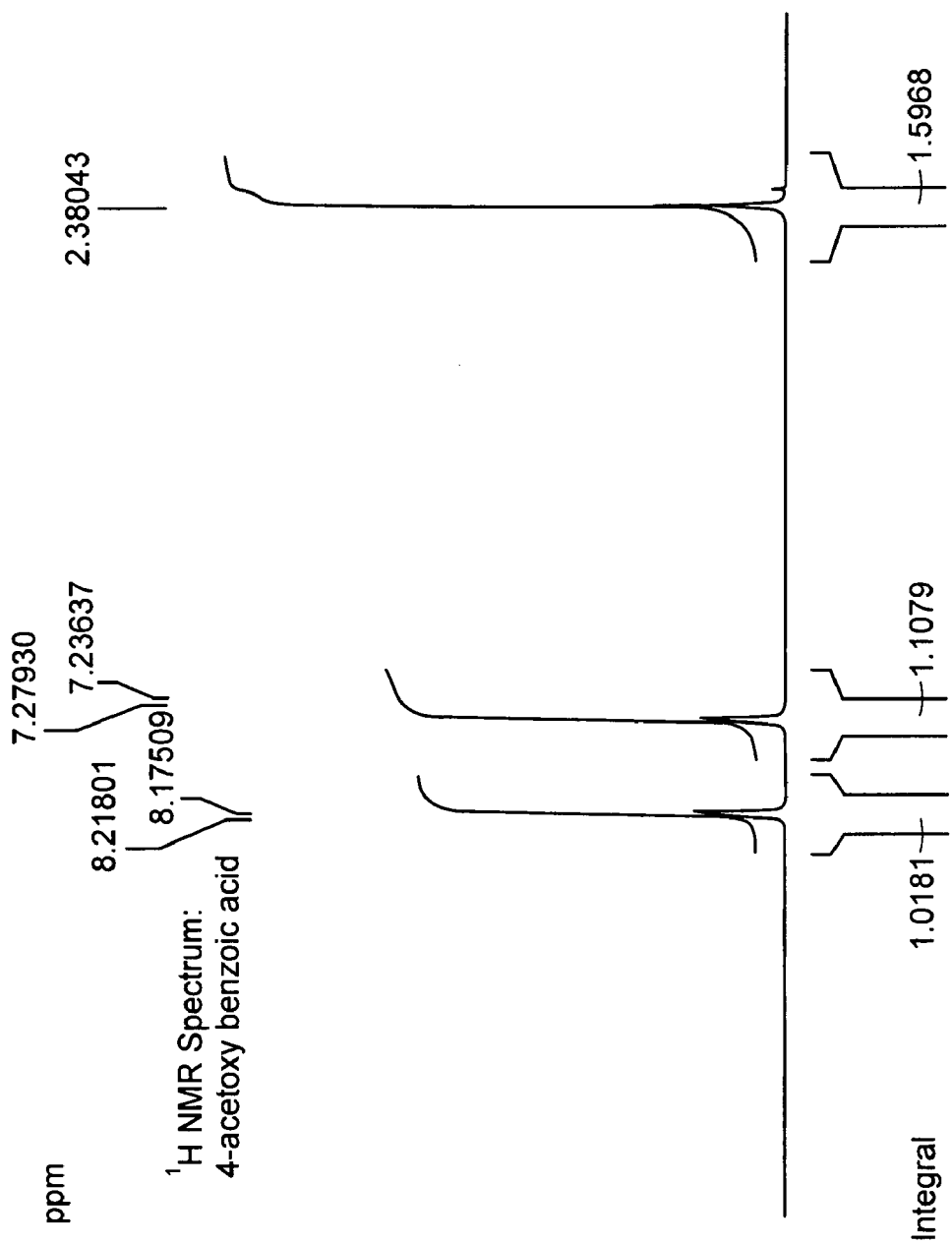
FIG. 1 depicts a) the $^1$H NMR spectrum of 4-acetoxy benzoic acid, b) the $^1$H NMR spectrum of 3,5-di-tert-butyl-4-hydroxy benzyl alcohol, c) the $^1$H NMR spectrum of the macromonomer formed from 4-acetoxy benzoic acid and 3,5-di-tert-butyl-4-hydroxy benzyl alcohol (compound 1), d) the $^1$H NMR spectrum of the macromonomer formed from deacetylation of acetylated monomer (compound 1), and e) the $^1$H NMR spectrum of macromonomer 6.

The present invention relates to macromonomer compounds possessing antioxidant properties, antioxidant polymers comprising the antioxidant macromonomers as a recurring unit, and methods of inhibiting oxidation in a substance comprising contacting the substance with the antioxidant polymers. In one embodiment, substantially all of the recurring macromonomeric units of the antioxidant polymers comprise an antioxidant moiety. In another embodiment, all of the recurring macromonomer units of the antioxidant polymers comprise an antioxidant moiety. This is achieved by polymerizing macromonomers which comprise an antioxidant moiety already, as opposed to polymerizing monomers comprising active functional groups and then derivatizing the resulting polymer with antioxidant molecules. The latter method is inefficient because not all active functional groups are accessible for reaction within the interior mass of the polymeric chains. The method of the present invention, however, yields antioxidant polymers with substantially all of the recurring units comprising an antioxidant moiety. The inventors therefore disclose antioxidant polymers having greater bulk antioxidative properties than previously known.

In certain embodiments, the antioxidative polymers of the present invention have a greater antioxidative effect than an equal amount (ppm) of antioxidant monomers as measured by isothermal oxidative induction time (OIT). The increased effect can be by as much as 100, 150, 200, 250, 300, 350, 385, or 400%.

In other embodiments, compositions comprising the antioxidative polymers of the present invention are disclosed. These compositions are less prone to oxidation due to the presence of the antioxidative polymers. The compositions may also further comprise non-polymer antioxidants such as BHT. In this way both short term and longer term stability towards oxidation is achieved due to different diffusion rates of the large and small molecules.

These embodiments of the present invention, other embodiments, and their features and characteristics, will be apparent from the description, drawings and claims that follow.

DETAILED DESCRIPTION OF THE INVENTION

Definitions

For convenience, before further description of the present invention, certain terms employed in the specification, examples and appended claims are collected here. These definitions should be read in light of the remainder of the disclosure and understood as by a person of skill in the art. Unless defined otherwise, all technical and scientific terms used herein have the same meaning as commonly understood by a person of ordinary skill in the art.

The articles "a" and "an" are used herein to refer to one or to more than one (i.e. to at least one) of the grammatical object of the article. By way of example, "an element" means one element or more than one element.

The terms "comprise" and "comprising" are used in the inclusive, open sense, meaning that additional elements may be included.

The term "including" is used herein to mean "including but not limited to". "Including" and "including but not limited to" are used interchangeably.

The term "antioxidant" is art-recognized and refers to any of various compounds that are added to substances in order to reduce the effect of oxidation and the accompanying degradation of properties. Non-limiting examples of substances that utilize antioxidants include paints, plastics, gasoline, rubber, and food products.

The term "oxidation" is art-recognized and refers to any reaction in which one or more electrons are removed from a species, thus increasing its valence (oxidation state).

The term "radical" is art-recognized and refers to an electrically neutral or ionic group having one or more unpaired electrons.

The term "substance" is used herein to mean any physical entity, commonly homogeneous, that occurs in macroscopic amounts.

The term "polymer" is art-recognized and refers to a macromolecule comprising a repeating monomeric unit. The term "polymer" also encompasses copolymers.

The term "monomer" is art-recognized and refers to a compound that is able to combine in long chains with other like or unlike molecules to produce polymers. The terms "macromonomer" and "monomer" are considered functionally the same.

The term "homopolyer" is art-recognized and refers to a polymer derived by a single repeating monomer.

The term "copolymer" is art-recognized and refers to a polymer that is composed of polymer chains made up of two or more chemically different repeating units that can be in different sequences.

The phrase "bulky alkyl group" is used herein to mean an alkyl group branched alpha or beta to a group, such as a benzene ring. The bulky alkyl group may be branched twice alpha to a benzene ring (i.e., to form an alpha-tertiary carbon), such as in a t-butyl group. Other non-limiting examples of a bulky alkyl group include isopropyl, 2-butyl, 3-pentyl, 1,1-dimethlypropyl, 1-ethyl-1-methylpropyl, and 1,1-diethylpropyl.

The term "enzyme" is art-recognized and refers to a protein that catalyzes reactions without itself being permanently altered or destroyed.

The term "enzyme mimetic" is art-recognized and refers to any substance that mimics the activity of an enzyme.

The term "catalyst" is art-recognized and refers to any substance that affects the rate of a chemical reaction without itself being consumed ore essentially altered.

The term "synthetic" is art-recognized and refers to production by in vitro chemical or enzymatic synthesis.

The term "instructional material" or "instructions" includes a publication, a recording, a diagram, or any other medium of expression which can be used to communicate the usefulness of a subject composition described herein for a method of treatment or a method of making or using a subject composition. The instructional material may, for example, be affixed to a container which contains the composition or be shipped together with a container which contains the composition or be contained in a kit with the composition. Alternatively, the instructional material may be shipped separately from the container with the intention that the instructional material and the composition be used cooperatively by the recipient.

The terms "number average molecular weight", or "Mn", "weight average molecular weight", "Z-average molecular weight" and "viscosity average molecular weight" are art-recognized. When the term "molecular weight" or an exemplary molecular weight is described herein, the measure of molecular weight will be clear from the context and/or will include all applicable measures.

"Small molecule" is an art-recognized term. In certain embodiments, this term refers to a molecule which has a molecular weight of less than about 2000 amu, or less than about 1000 amu, and even less than about 500 amu.

The term "aliphatic" is an art-recognized term and includes linear, branched, and cyclic alkanes, alkenes, or alkynes. In certain embodiments, aliphatic groups in the present invention are linear or branched and have from 1 to about 20 carbon atoms.

The term "alkyl" is art-recognized, and includes saturated aliphatic groups, including straight-chain alkyl groups, branched-chain alkyl groups, cycloalkyl(alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., $C_1$-$C_{30}$ for straight chain, $C_3$-$C_{30}$ for branched chain), and alternatively, about 20 or fewer. Likewise, cycloalkyls have from about 3 to about 10 carbon atoms in their ring structure, and alternatively about 5, 6 or 7 carbons in the ring structure. The term "alkyl" is also defined to include halosubstituted alkyls.

The term "aralkyl" is art-recognized, and includes alkyl groups substituted with an aryl group (e.g., an aromatic or heteroaromatic group).

The terms "alkenyl" and "alkynyl" are art-recognized, and include unsaturated aliphatic groups analogous in length and possible substitution to the alkyls described above, but that contain at least one double or triple bond respectively.

Unless the number of carbons is otherwise specified, "lower alkyl" refers to an alkyl group, as defined above, but having from one to ten carbons, alternatively from one to about six carbon atoms in its backbone structure. Likewise, "lower alkenyl" and "lower alkynyl" have similar chain lengths.

The term "heteroatom" is art-recognized, and includes an atom of any element other than carbon or hydrogen. Illustrative heteroatoms include boron, nitrogen, oxygen, phosphorus, sulfur and selenium, and alternatively oxygen, nitrogen or sulfur.

The term "aryl" is art-recognized, and includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" "heteroaryls," or "heteroaromatics." The aromatic ring may be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, aryls and/or heterocyclyls.

The terms ortho, meta and para are art-recognized and apply to 1,2-, 1,3- and 1,4-disubstituted benzenes, respectively. For example, the names 1,2-dimethylbenzene and ortho-dimethylbenzene are synonymous.

The terms "heterocyclyl" and "heterocyclic group" are art-recognized, and include 3- to about 10-membered ring structures, such as 3- to about 7-membered rings, whose ring structures include one to four heteroatoms. Heterocycles may also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring may be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The terms "polycyclyl" and "polycyclic group" are art-recognized, and include structures with two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms, e.g., three or more atoms are common to both rings, are termed "bridged" rings. Each of the rings of the polycycle may be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The term "carbocycle" is art recognized and includes an aromatic or non-aromatic ring in which each atom of the ring is carbon. The flowing art-recognized terms have the following meanings: "nitro" means —$NO_2$; the term "halogen" designates —F, —Cl, —Br or —I; the term "sulfhydryl" means —SH; the term "hydroxyl" means —OH; and the term "sulfonyl" means —$SO_2^-$.

The terms "amine" and "amino" are art-recognized and include both unsubstituted and substituted amines, e.g., a moiety that may be represented by the general formulas:

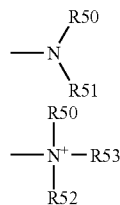

wherein R50, R51 and R52 each independently represent a hydrogen, an alkyl, an alkenyl, —$(CH_2)_m$—R61, or R50 and R51, taken together with the N atom to which they are attached complete a heterocycle having from 4 to 8 atoms in the ring structure; R61 represents an aryl, a cycloalkyl, a cycloalkenyl, a heterocycle or a polycycle; and m is zero or an integer in the range of 1 to 8. In certain embodiments, only one of R50 or R51 may be a carbonyl, e.g., R50, R51 and the nitrogen together do not form an imide. In other embodiments, R50 and R51 (and optionally R52) each independently represent a hydrogen, an alkyl, an alkenyl, or —$(CH_2)_m$—R61. Thus, the term "alkylamine" includes an amine group, as defined above, having a substituted or unsubstituted alkyl attached thereto, i.e., at least one of R50 and R51 is an alkyl group.

The term "acylamino" is art-recognized and includes a moiety that may be represented by the general formula:

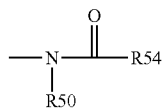

wherein R50 is as defined above, and R54 represents a hydrogen, an alkyl, an alkenyl or —$(CH_2)_m$—R61, where m and R61 are as defined above.

The term "amido" is art recognized as an amino-substituted carbonyl and includes a moiety that may be represented by the general formula:

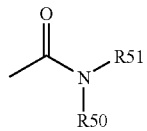

wherein R50 and R51 are as defined above. Certain embodiments of the amide in the present invention will not include imides which may be unstable.

The term "alkylthio" is art recognized and includes an alkyl group, as defined above, having a sulfur radical attached thereto. In certain embodiments, the "alkylthio" moiety is represented by one of —S-alkyl, —S-alkenyl, —S-alkynyl, and —S—$(CH_2)_m$—R61, wherein m and R61 are defined above. Representative alkylthio groups include methylthio, ethyl thio, and the like.

The term "carbonyl" is art recognized and includes such moieties as may be represented by the general formulas:

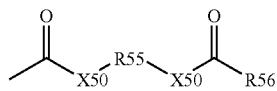

wherein X50 is a bond or represents an oxygen or a sulfur, and R5 represents a hydrogen, an alkyl, an alkenyl, —$(CH_2)_m$—R61 or a pharmaceutically acceptable salt, R56 represents a hydrogen, an alkyl, an alkenyl or —$(CH_2)$, —R61, where m and R61 are defined above. Where X50 is an oxygen and R55 or R56 is not hydrogen, the formula represents an "ester". Where X50 is an oxygen, and R55 is as defined above, the moiety is referred to herein as a carboxyl group, and particularly when R55 is a hydrogen, the formula represents a "carboxylic acid". Where X50 is an oxygen, and R56 is hydrogen, the formula represents a "formate". In general, where the oxygen atom of the above formula is replaced by sulfur, the formula represents a "thiocarbonyl" group. Where X50 is a sulfur and R55 or R56 is not hydrogen, the formula represents a "thioester." Where X50 is a sulfur and R55 is hydrogen, the formula represents a "thiocarboxylic acid." Where X50 is a sulfur and R56 is hydrogen, the formula represents a "thioformate." On the other hand, where X50 is a bond, and R55 is not hydrogen, the above formula represents a "ketone" group. Where X50 is a bond, and R55 is hydrogen, the above formula represents an "aldehyde" group.

The terms "alkoxyl" or "alkoxy" are art recognized and include an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, —O—(CH$_2$)$_m$—R61, where m and R61 are described above.

The term "sulfonate" is art recognized and includes a moiety that may be represented by the general formula:

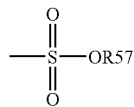

in which R57 is an electron pair, hydrogen, alkyl, cycloalkyl, or aryl.

The term "sulfate" is art recognized and includes a moiety that may be represented by the general formula:

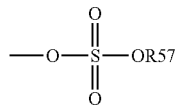

in which R57 is as defined above.

The term "sulfonamido" is art recognized and includes a moiety that may be represented by the general formula:

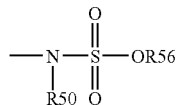

in which R50 and R56 are as defined above.

The term "sulfamoyl" is art-recognized and includes a moiety that may be represented by the general formula:

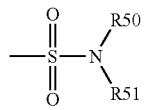

in which R50 and R51 are as defined above.

The term "sulfonyl" is art recognized and includes a moiety that may be represented by the general formula:

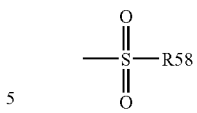

in which R58 is one of the following: hydrogen, alkyl, alkenyl, alkynyl, cycloalkyl, heterocyclyl, aryl or heteroaryl.

The term "sulfoxido" is art recognized and includes a moiety that may be represented by the general formula:

in which R58 is defined above.

The term "phosphoramidite" is art recognized and includes moieties represented by the general formulas:

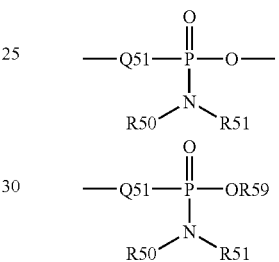

wherein Q51, R50, R51 and R59 are as defined above.

The term "phosphonamidite" is art recognized and includes moieties represented by the general formulas:

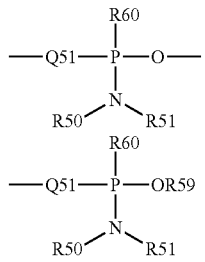

wherein Q51, R50, R51 and R59 are as defined above, and R60 represents a lower alkyl or an aryl.

Analogous substitutions may be made to alkenyl and alkynyl groups to produce, for example, aminoalkenyls; aminoalkynyls, amidoalkenyls, amidoalkynyls, iminoalkenyls, iminoalkynyls, thioalkenyls, thioalkynyls, carbonyl-substituted alkenyls or alkynyls.

The definition of each expression, e.g. alkyl, m, n, etc., when it occurs more than once in any structure, is intended to be independent of its definition elsewhere in the same structure unless otherwise indicated expressly or by the context.

The term "selenoalkyl" is art recognized and includes an alkyl group having a substituted seleno group attached thereto. Exemplary "selenoethers" which may be substituted on the alkyl are selected from one of —Se-alkyl, —Se-alkenyl, —Se-alkynyl, and —Se—(CH$_2$)$_m$—R61, m and R61 being defined above.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, and Ms are art recognized and represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the Journal of Organic Chemistry; this list is typically presented in a table entitled *Standard List of Abbreviations*.

Certain monomeric subunits of the present invention may exist in particular geometric or stereoisomeric forms. In addition, polymers and other compositions of the present invention may also be optically active. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically active acid or base, followed by resolution of the diastereomers thus formed by fractional crystallization or chromatographic means well known in the art, and subsequent recovery of the pure enantiomers.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

For purposes of this invention, the chemical elements are identified in accordance with the Periodic Table of the Elements, CAS version, Handbook of Chemistry and Physics, 67th Ed., 1986-87, inside cover. The term "hydrocarbon" is art recognized and includes all permissible compounds having at least one hydrogen and one carbon atom. For example, permissible hydrocarbons include acyclic and cyclic, branched and unbranched, carbocyclic and heterocyclic, aromatic and nonaromatic organic compounds that may be substituted or unsubstituted.

The phrase "protecting group" is art recognized and includes temporary substituents that protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed. Greene et al., *Protective Groups in Organic Synthesis* 2$^{nd}$ ed., Wiley, New York, (1991).

The phrase "hydroxyl-protecting group" is art recognized and includes those groups intended to protect a hydroxyl group against undesirable reactions during synthetic procedures and includes, for example, benzyl or other suitable esters or ethers groups known in the art.

The term "electron-withdrawing group" is recognized in the art, and denotes the tendency of a substituent to attract valence electrons from neighboring atoms, i.e., the substituent is electronegative with respect to neighboring atoms. A quantification of the level of electron-withdrawing capability is given by the Hammett sigma ($\sigma$) constant. This well known constant is described in many references, for instance, March, *Advanced Organic Chemistry* 251-59, McGraw Hill Book Company, New York, (1977). The Hammett constant values are generally negative for electron donating groups ($\sigma(P)=-0.66$ for $NH_2$) and positive for electron withdrawing groups ($\sigma(P)=0.78$ for a nitro group), $\sigma(P)$ indicating para substitution. Exemplary electron-withdrawing groups include nitro, acyl, formyl, sulfonyl, trifluoromethyl, cyano, chloride, and the like. Exemplary electron-donating groups include amino, methoxy, and the like.

Contemplated equivalents of the polymers, subunits and other compositions described above include such materials which otherwise correspond thereto, and which have the same general properties thereof (e.g., biocompatible), wherein one or more simple variations of substituents are made which do not adversely affect the efficacy of such molecule to achieve its intended purpose. In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants which are in themselves known, but are not mentioned here.

Macromonomer Antioxidants and Antioxidant Polymers

In part, the present invention relates to a compound having formula I:

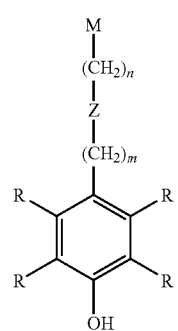

I wherein, independently for each occurrence,
n and m are integers from 0 to 18, inclusive;
Z is —C(O)O—, —OC(O)—, —C(O)NH—, —NHC(O)—, —NH—, —CH=N—, —N=CH—, —C(O)—, —O—, —S—, —S—S—, —S=N—, —N=S—, —C(S)O—, —OC(S)—, —OP(O)(OR$_4$)O—, —OP(OR$_4$)O—, —C(O)OC(O)—, or a bond;
R is H, C$_{1-6}$ alkyl, —OH, —NH$_2$, —SH, aryl, ester, or

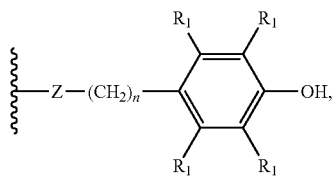

wherein at least one R adjacent to the —OH group is a bulky alkyl group;
R$_1$ is H, C$_{1-6}$ alkyl, aryl, aralkyl, —OH, —NH$_2$, —SH, or ester wherein at least one R$_1$ adjacent to the —OH group is a bulky alkyl group;
R$_4$ is H, C$_{1-6}$ alkyl, aryl, aralkyl, heteroaryl, or heteroaralkyl; and

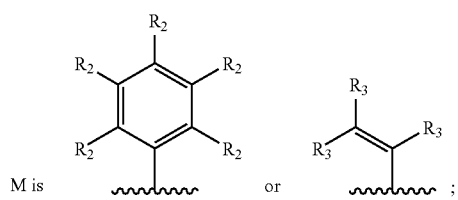

wherein
R$_2$ is H, C$_{1-6}$ alkyl, —OH, —NH$_2$, —SH, aryl, ester, or

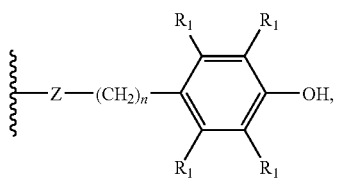

wherein at least one R$_2$ is —OH; and
R$_3$ is H, C$_{1-6}$ alkyl, aryl, aralkyl, —OH, —NH$_2$, —SH, or ester.

In another embodiment, the present invention relates to a compound of formula I and the attendant definitions, wherein Z is —OC(O)—. In another embodiment, Z is —C(O)O—. In another embodiment, Z is —C(O)NH—. In another embodiment, Z is —NHC(O)—. In another embodiment, Z is —NH—. In another embodiment, Z is —CH=N—. In another embodiment, Z is —N=CH—. In another embodiment, Z is —C(O)—. In another embodiment, Z is —O—. In another embodiment, Z is —C(O)OC(O)—. In another embodiment, Z is —S—. In another embodiment, Z is —S—S—. In another embodiment, Z is —S=N—. In another embodiment, Z is —N=S—. In another embodiment, Z is —C(S)O—. In another embodiment, Z is —OC(S)—. In another embodiment, Z is —OP(O)(OR$_4$)O—. In another embodiment, Z is —OP(OR$_4$)O—. In another embodiment, Z is a bond.

In another embodiment, the present invention relates to a compound of formula I and the attendant definitions, wherein both R groups adjacent to —OH are bulky alkyl groups. In another embodiment, both R groups are t-butyl.

In another embodiment, the present invention relates to a compound of formula I and the attendant definitions, wherein M is

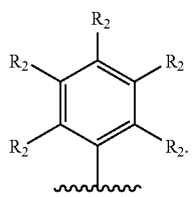

In another embodiment, the present invention relates to a compound of formula I and the attendant definitions, wherein M is

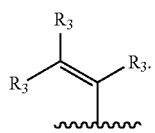

In another embodiment, the present invention relates to a compound of formula I and the attendant definitions, wherein at least one R is

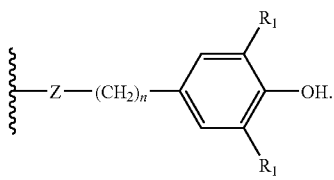

In another embodiment, the present invention relates to a compound of formula I and the attendant definitions, wherein n is 0.

In another embodiment, the present invention relates to a compound of formula I and the attendant definitions, wherein m is 1.

In another embodiment, the present invention relates to a compound of formula I and the attendant definitions, wherein n is 0 and m is 1.

In another embodiment, the present invention relates to a compound of formula I and the attendant definitions, wherein n is 0, m is 1, and Z is —C(O)O—.

In another embodiment, the present invention relates to a compound of formula I and the attendant definitions, wherein n is 0, m is 1, Z is —C(O)O—, and the two R groups adjacent to the OH are t-butyl.

In another embodiment, the present invention relates to a compound of formula I and the attendant definitions, wherein n is 0, m is 1, Z is —C(O)O—, the two R groups adjacent to the OH are t-butyl, and M is

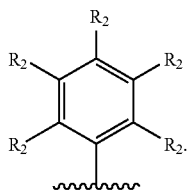

In another embodiment, the present invention relates to a compound of formula I and the attendant definitions, wherein n is 0, m is 1, Z is —C(O)O—, the two R groups adjacent to the OH are t-butyl, M is

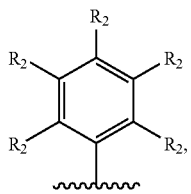

and the $R_2$ in the para position is OH.

In another embodiment, the present invention relates to a compound of formula I and the attendant definitions, wherein n is 0, m is 1, Z is —C(O)O—, the two R groups adjacent to the OH are t-butyl, M is

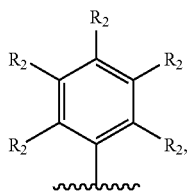

the $R_2$ in the para position is OH, and an adjacent $R_2$ is OH.

In another embodiment, the present invention relates to a compound of formula I and the attendant definitions, wherein n is 0, m is 1, Z is —C(O)O—, the two R groups adjacent to the OH are t-butyl, M is

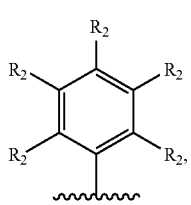

the $R_2$ in the para position is OH, and the two adjacent $R_2$'s are OH.

In another embodiment, the present invention relates to a compound of formula I and the attendant definitions, wherein n is 0, m is 1, Z is —C(O)O—, the two R groups adjacent to the OH are t-butyl, and M is

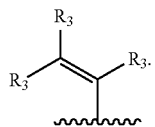

In a further embodiment, the present invention relates to a compound of formula I and the attendant definitions, wherein n is 0, m is 1, Z is —C(O)O—, the two R groups adjacent to the OH are t-butyl, M is

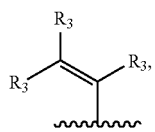

and $R_3$ is H.

In part, the present invention relates to a polymer wherein substantially all the recurring monomeric units comprise an antioxidant moiety. In a further embodiment, all the recurring monomeric units comprise an antioxidant moiety.

In part, the present invention relates to a polymer wherein substantially all the recurring monomeric units comprise an antioxidant moiety, wherein the recurring monomeric unit is a benzene ring substituted with an antioxidant moiety. In another embodiment, the recurring monomeric unit is an alkenylene substituted with an antioxidant moiety.

In part, the present invention relates to a polymer wherein substantially all the recurring monomeric units comprise an antioxidant moiety, wherein the antioxidant moiety comprises a hydroxy substituted benzene ring. In a further embodiment, the benzene ring is substituted with at least one bulky alkyl group. In a further embodiment, the bulky alkyl group is a t-butyl group. In a further embodiment, the t-butyl group is adjacent to the hydroxy group. In a further embodiment, the benzene ring is substituted with 2 t-butyl groups adjacent to the hydroxy group.

In part, the present invention relates to a polymer comprising at least one recurring monomeric unit shown in formula II:

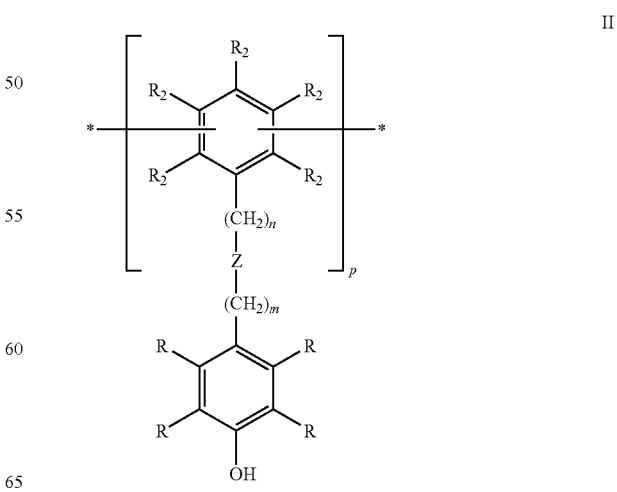

II wherein, independently for each occurrence,
n and m are integers from 0 to 18, inclusive;
p is an integer equal to or greater than 2;
Z is —C(O)O—, —OC(O)—, —C(O)NH—, —NHC(O)—, —NH—, —CH═N—, —N═CH—, —C(O)—, —O—, —S—, —S—S—, —S═N—, —N═S—, —C(S)O—, —OC(S)—, —OP(O)(OR$_3$)$_o$—, —OP(OR$_3$)O—, —C(O)OC(O)—, or a bond;
R is H, C$_{1-6}$ alkyl, OH, —NH$_2$, —SH, aryl, ester, or

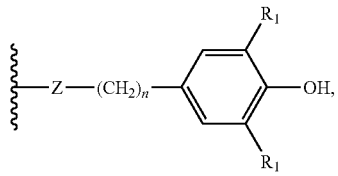

wherein at least one R adjacent to the —OH group is a bulky alkyl group;
R$_1$ is H or C$_{1-6}$ alkyl, —OH, —NH$_2$, —SH, aryl, or ester wherein at least one R1 is a bulky alkyl group;
R$_2$ is H, C$_{1-6}$ alkyl, aryl, aralkyl, —OH, —NH$_2$, —SH, ester, or

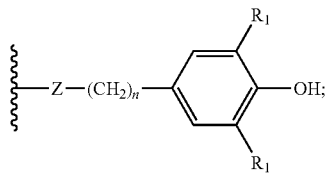

and
R$_3$ is H, C$_{1-6}$ alkyl, aryl, aralkyl, heteroaryl, or heteroaralkyl,
wherein substantially all of the recurring monomeric units comprise an antioxidant moiety. In a further embodiment, all the recurring monomeric units comprise an antioxidant moiety.

In another embodiment, the present invention relates to a polymer comprising at least one recurring monomeric unit shown in formula II and the attendant definitions, wherein Z is —C(O)O—. In another embodiment, Z is —OC(O)—. In another embodiment, Z is —C(O)NH—. In another embodiment, Z is —NHC(O)—. In another embodiment, Z is —NH—. In another embodiment, Z is —CH═N—. In another embodiment, Z is —N═CH—. In another embodiment, Z is —C(O)—. In another embodiment, Z is —O—. In another embodiment, Z is —C(O)OC(O)—. In another embodiment, Z is —S—. In another embodiment, Z is —S—S—. In another embodiment, Z is —S═N—. In another embodiment, Z is —N═S—. In another embodiment, Z is —C(S)O—. In another embodiment, Z is —OC(S)—. In another embodiment, Z is —OP(O)(OR$_4$)O—. In another embodiment, Z is —OP(OR$_4$)O—. In another embodiment, Z is a bond.

In another embodiment, the present invention relates to a polymer comprising at least one recurring monomeric unit shown in formula II and the attendant definitions, wherein both R groups adjacent to —OH are bulky alkyl groups. In a further embodiment, the R groups adjacent to —OH are t-butyl.

In another embodiment, the present invention relates to a polymer comprising at least one recurring monomeric unit shown in formula II and the attendant definitions, wherein at least one R group is

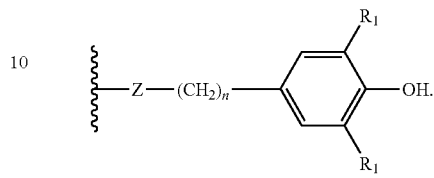

In another embodiment, the present invention relates to a polymer comprising at least one recurring monomeric unit shown in formula II and the attendant definitions, wherein the R$_2$ in the para position is —OH.

In another embodiment, the present invention relates to a polymer comprising at least one recurring monomeric unit shown in formula II and the attendant definitions, wherein n is 0.

In another embodiment, the present invention relates to a polymer comprising at least one recurring monomeric unit shown in formula H and the attendant definitions, wherein m is 1.

In another embodiment, the present invention relates to a polymer comprising at least one recurring monomeric unit shown in formula II and the attendant definitions, wherein n is 0 and m is 1.

In another embodiment, the present invention relates to a polymer comprising at least one recurring monomeric unit shown in formula II and the attendant definitions, wherein n is 0, m is 1, and Z is —C(O)O—.

In another embodiment, the present invention relates to a polymer comprising at least one recurring monomeric unit shown in formula II and the attendant definitions, wherein n is 0, m is 1, Z is —C(O)O—, and the two R groups adjacent to the OH are t-butyl.

In another embodiment, the present invention relates to a polymer comprising at least one recurring monomeric unit shown in formula II and the attendant definitions, wherein n is 0, m is 1, Z is —C(O)O—, the two R groups adjacent to the OH are t-butyl, and the R$_2$ in the para position is OH.

In another embodiment, the present invention relates to a polymer comprising at least one recurring monomeric unit shown in formula II and the attendant definitions, wherein n is 0, m is 1, Z is —C(O)O—, the two R groups adjacent to the OH are t-butyl, the R$_2$ in the para position is OH, and an adjacent R$_2$ is —OH.

In another embodiment, the present invention relates to a polymer comprising at least one recurring monomeric unit shown in formula II and the attendant definitions, wherein n is 0, m is 1, Z is —C(O)O—, the two R groups adjacent to the OH are t-butyl, the R$_2$ in the para position is OH, and the two adjacent R$_2$'s are —OH.

In part, the present invention relates to a polymer comprising the recurring monomeric unit shown in formula III:

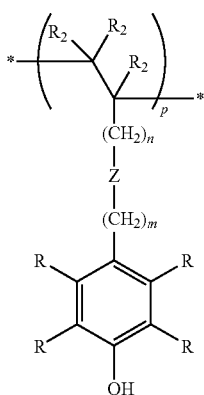

wherein, independently for each occurrence,
n and m are integers from 0 to 18, inclusive;
p is an integer of at least 2;
Z is —C(O)O—, —OC(O)—, —C(O)NH—, —NHC(O)—, —NH—, —CH=N—, —N=CH—, —C(O)—, —O—, —S—, —S—S—, —S=N—, —N=S—, —C(S)O—, —OC(S)—, —OP(O)(OR$_3$)O—, —OP(OR$_3$)O—, —C(O)OC(O)—, or a bond;
R is H, C$_{1-6}$ alkyl, —OH, —NH$_2$, —SH, aryl, ester, or

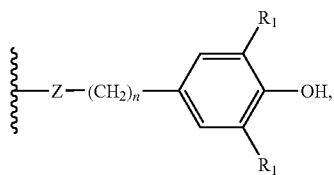

wherein at least one R adjacent to the —OH group is a bulky alkyl group;
R$_1$ is H or C$_{1-6}$ alkyl, —OH, —NH$_2$, —SH, aryl, or ester wherein at least one R$_1$ is a bulky alkyl group;
R$_2$ is H, C$_{1-6}$ alkyl, aryl, aralkyl, —OH, —NH$_2$, —SH, or ester; and
R$_3$ is H, C$_{1-6}$ alkyl, aryl, aralkyl, heteroaryl, or heteroalkyl,
wherein substantially all of the recurring monomeric units comprise an antioxidant moiety. In a further embodiment, all recurring monomeric units comprise an antioxidant moiety.

In a further embodiment, the present invention relates to a polymer comprising the recurring monomeric unit shown in formula III and the attendant definitions, wherein Z is —C(O)O—. In another embodiment, Z is —OC(O)—. In another embodiment, Z is —C(O)NH—. In another embodiment, Z is —NHC(O)—. In another embodiment, Z is —NH—. In another embodiment, Z is —CH=N—. In another embodiment, Z is —N=CH—. In another embodiment, Z is —C(O)—. In another embodiment, Z is —O—. In another embodiment, Z is —C(O)OC(O)—. In another embodiment, Z is —S—. In another embodiment, Z is —S—S—. In another embodiment, Z is —S=N—. In another embodiment, Z is —N=S—. In another embodiment, Z is —C(S)O—. In another embodiment, Z is —OC(S)—. In another embodiment, Z is —OP(O)(OR$_4$)O—. In another embodiment, Z is —OP(OR$_4$)O—. In another embodiment, Z is a bond.

In another embodiment, the present invention relates to a polymer comprising the recurring monomeric unit shown in formula III and the attendant definitions, wherein both R groups adjacent to —OH are bulky alkyl groups. In a further embodiment, both R groups adjacent to —OH are t-Bu.

In another embodiment, the present invention relates to a polymer comprising the recurring monomeric unit shown in formula III and the attendant definitions, wherein at least one R is

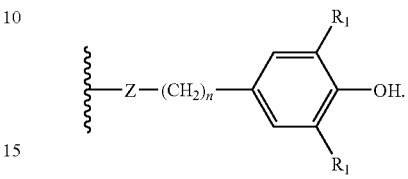

In another embodiment, the present invention relates to a polymer comprising the recurring monomeric unit shown in formula III and the attendant definitions, wherein n is 0.

In another embodiment, the present invention relates to a polymer comprising the recurring monomeric unit shown in formula III and the attendant definitions, wherein m is 1.

In another embodiment, the present invention relates to a polymer comprising the recurring monomeric unit shown in formula III and the attendant definitions, wherein n is 0 and m is 1.

In another embodiment, the present invention relates to a polymer comprising the recurring monomeric unit shown in formula III and the attendant definitions, wherein n is 0, m is 1, and Z is —C(O)O—.

In another embodiment, the present invention relates to a polymer comprising the recurring monomeric unit shown in formula III and the attendant definitions, wherein n is 0, m is 1, Z is —C(O)O—, and the two R groups adjacent to the —OH are t-butyl.

In another embodiment, the present invention relates to a polymer comprising the recurring monomeric unit shown in formula III and the attendant definitions, wherein n is 0, m is 1, Z is —C(O)O—, the two R groups adjacent to the —OH are t-butyl, and R$_2$ is H.

In part the present invention relates to copolymers comprising the recurring monomeric units of formulas II or III. The other recurring monomeric units may or may not comprise an antioxidative moiety.

In part, the present invention also relates to a method of inhibiting oxidation of a substance comprising contacting the substance with the antioxidant polymers of the present invention.

Synthesis of Macromonomer Antioxidants

The macromonomer antioxidants of the present invention may be prepared by several different methods and starting materials. The following are synthetic routes to formation of the macromonomer antioxidants: 1) esterification, 2) amidification, 3) ketone formation, 4) alkylation, and 5) anhydride formation.

1) Esterification

In this approach, two molecules or more possessing antioxidant properties are used to form a macromolecular antioxidant molecule through an esterification process. Suitable antioxidant-acid type molecule and/or antioxidant-alcohol type molecule are coupled to form an ester linkage by one of the following methods: a) chemical routes b) enzymatic routes, and c) chemoenzymatic routes.

a) Chemical Routes

Scheme 1 depicts the chemical coupling of acid chloride with antioxidant-alcohol in the presence of base like triethyl amine followed by deacetylation to form a macromonomer of the present invention.

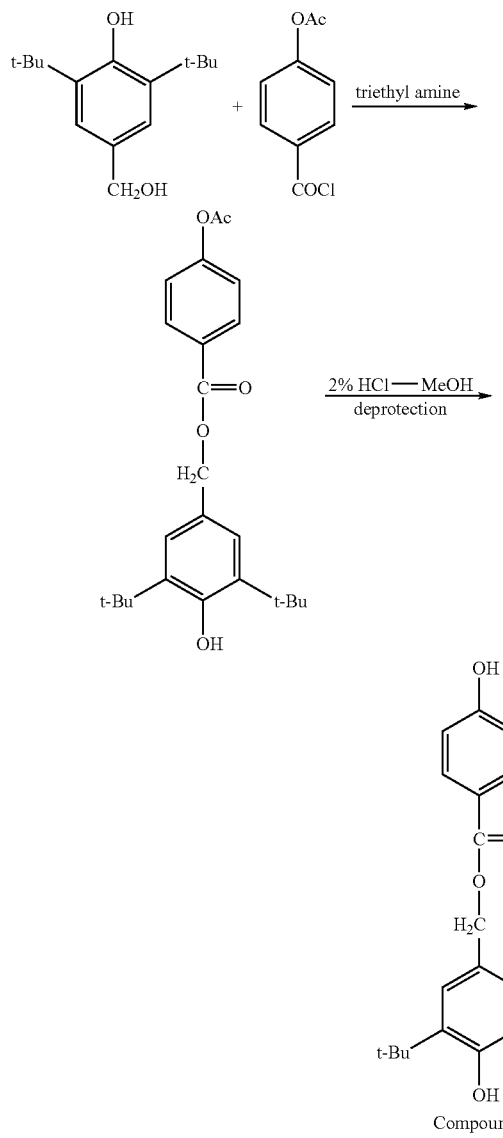

Figure 1B:
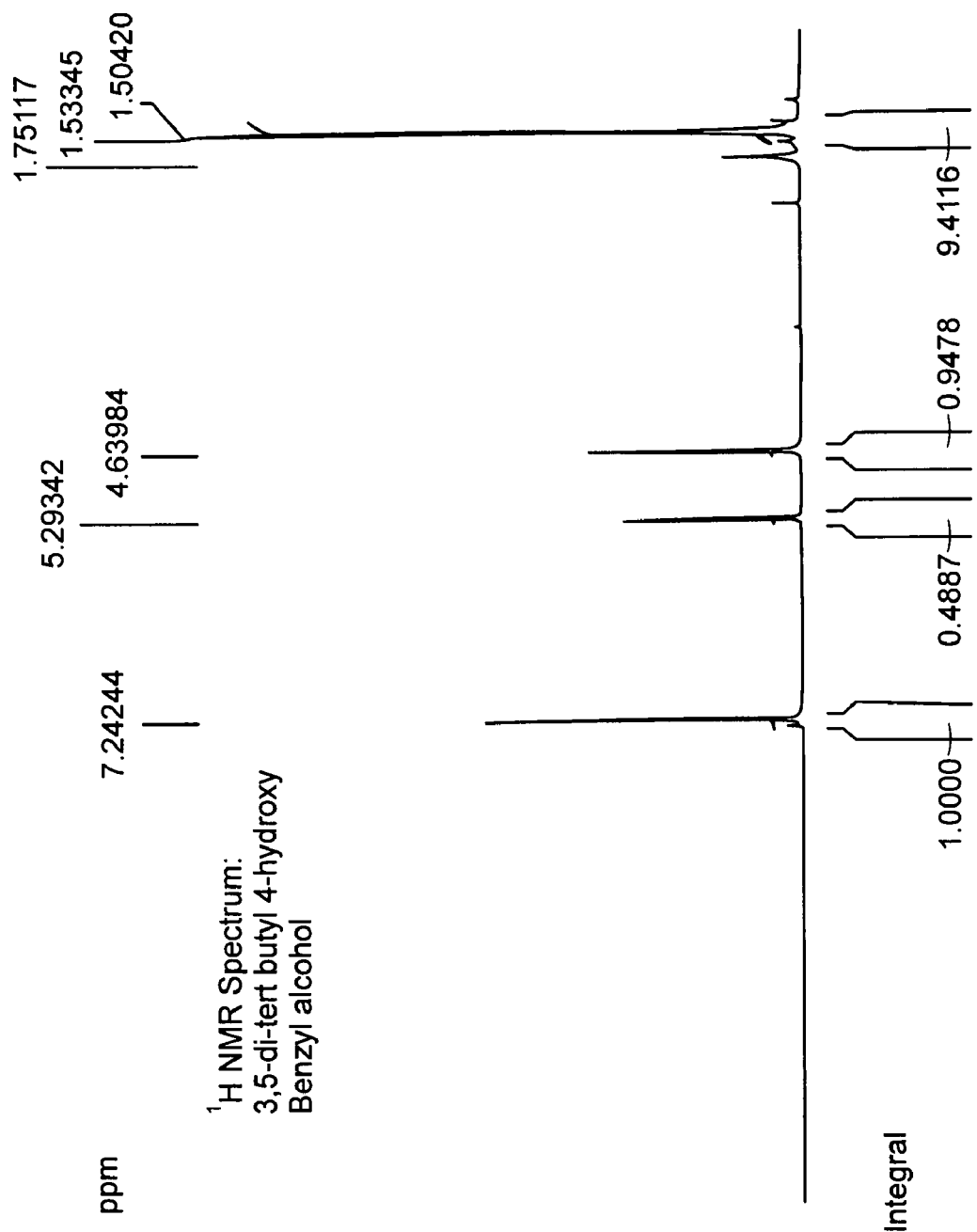
Figure 1C:
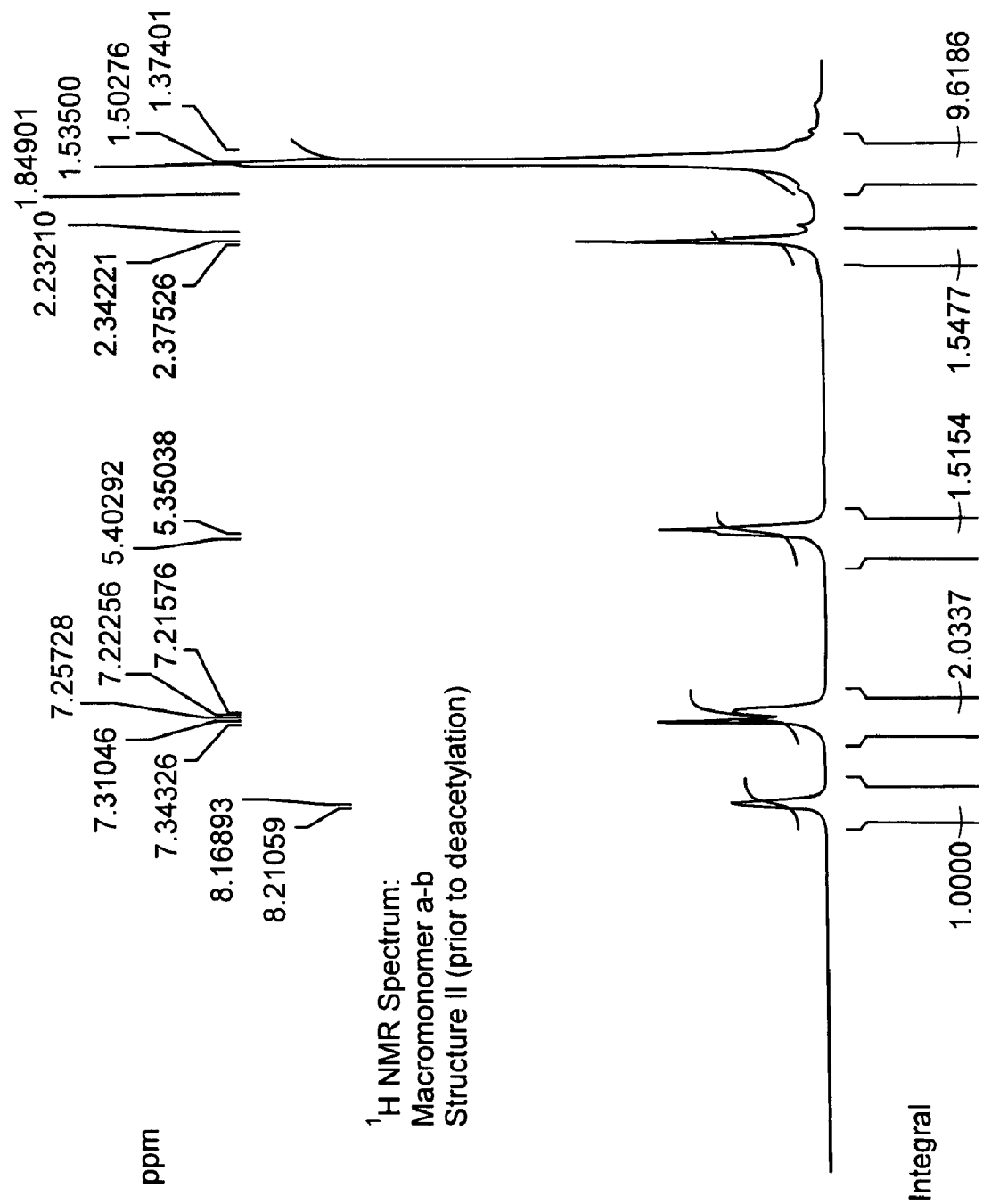
Figure 1D:
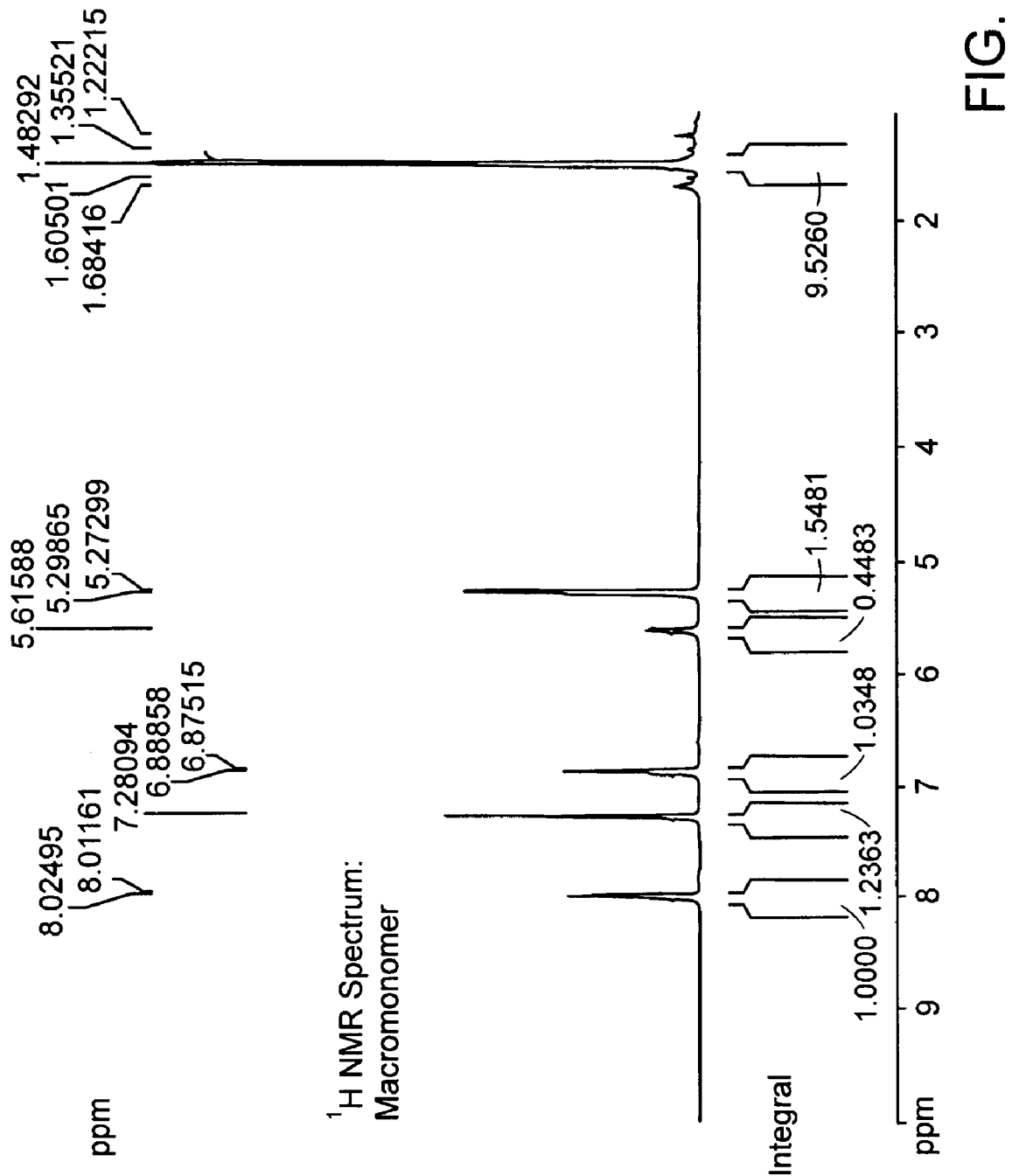
Figure 1E:
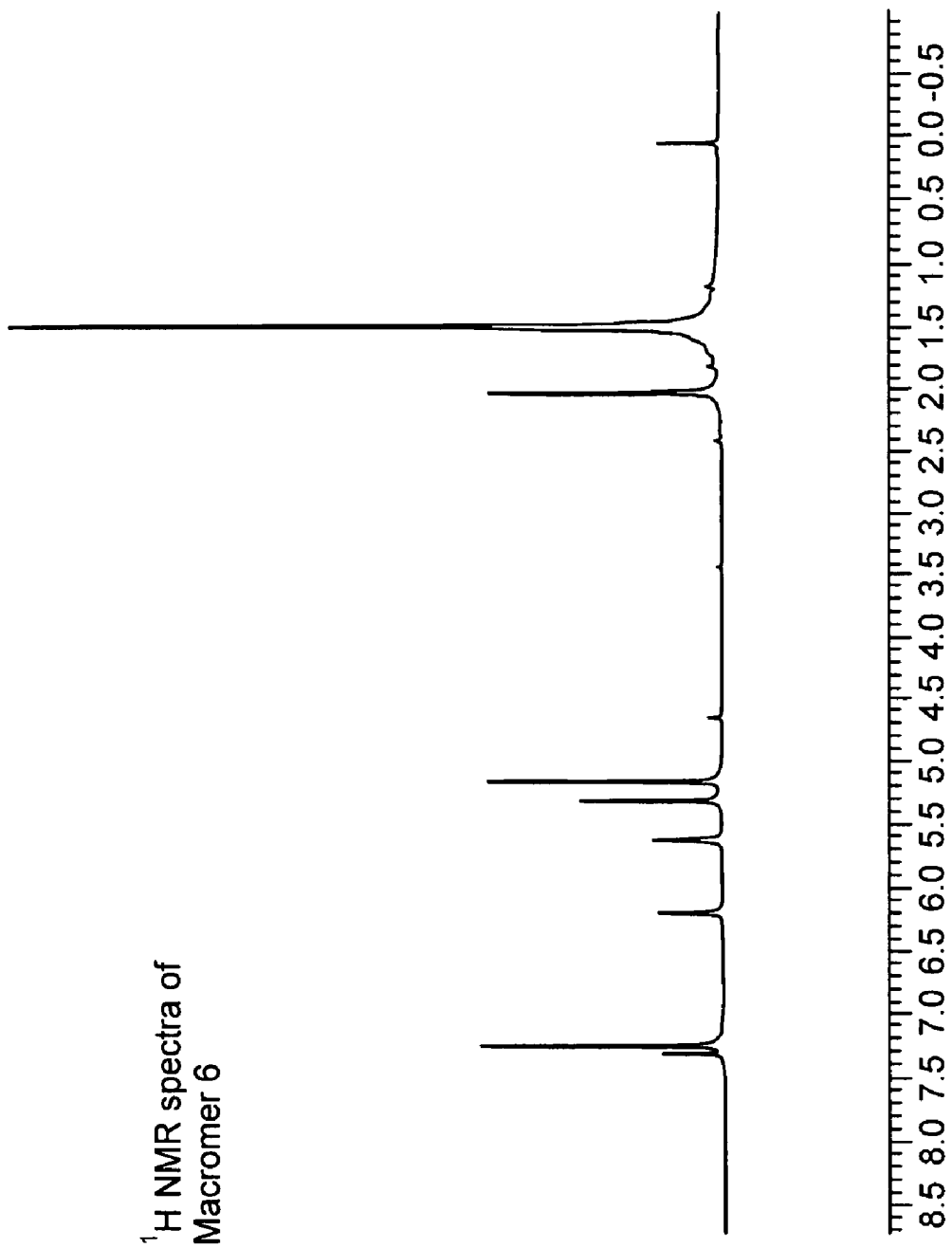

$^1$H NMR characterization is depicted in FIGS. 1a-1c. Formation of an ester linkage is clearly evident from the shift of benzylic protons from 4.6 ppm in alcohol to 5.35 ppm in the acetylated ester product and disappearance of acidic proton of 4-acetoxy benzoic acid at 10 ppm in the product (FIG. 1a). The disappearance of acetoxy peaks at 2.3 ppm in FIG. 1b is the indication of deacetylation of the final product.

Alternatively, macromonomer compound 1 and analogs thereof may be prepared by refluxing the mixture of 4-hydroxy benzoic acid and 3,5 di-tert-butyl-4-hydroxy-benzyl alcohol in toluene in presence of anhydrous para-toluene sulponic acid. Journal of Natural Products, 2003, Vol. 66, No. 5.

Another possible chemical synthetic approach for the formation of compound 1 and analogs thereof is the esterification of 4-hydroxy-benzoic acid with 3,5 di-tert-butyl-4-hydroxy-toulene (BHT) using sodium bromate and sodium hydrogen sulphite at ambient temperature under a two phase systems as depicted in Scheme 2. Tetrahedron 59 (2003) 5549-5554.

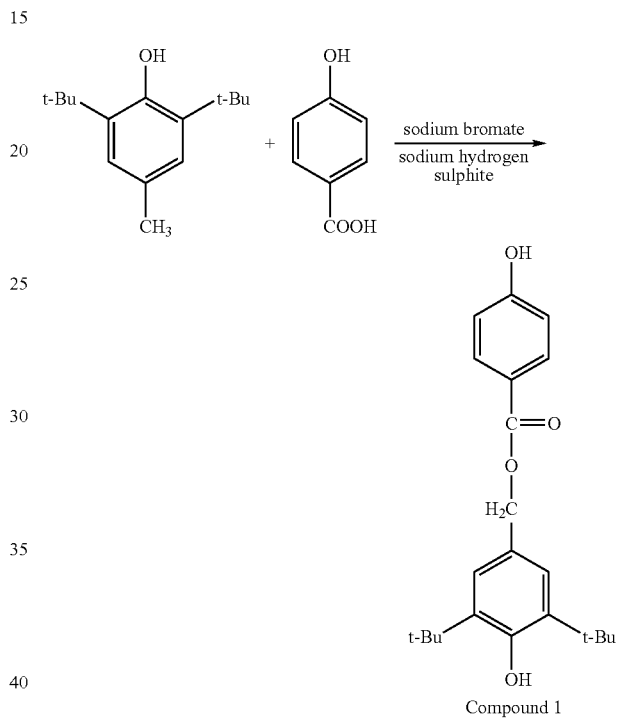

Analogs of compound 1 can be prepared by the above methods starting with 3,4-dihydroxy benzoic acid and 3,4,5-trihydroxybenzoic acid (Gallic acid) and are depicted below as compounds 2 and 3, respectively, or by coupling 4-hydroxy-benzyl alcohol and 3,5-di-tert-butyl-4-hydroxy-propionyl chloride to yield compound 4.

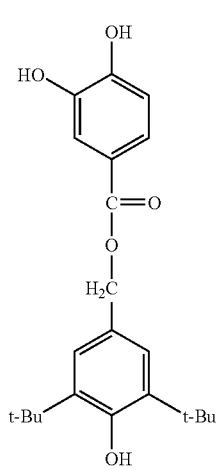

Compound 2

Compound 3

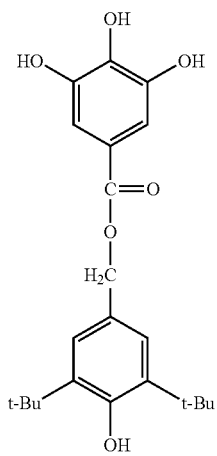

Compound 4

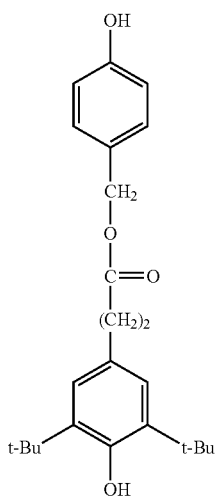

b) Enzymatic Routes

The general scheme for the synthesis of macromonomer antioxidant molecules either in bulk or solvent medium using lipase as a biocatalyst is presented in Scheme 3.

Scheme 3.
Enzymatic routes to marcomonomer antioxidants.

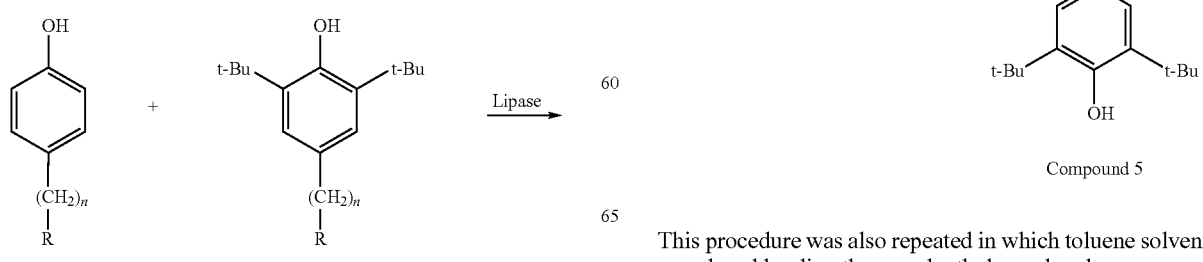

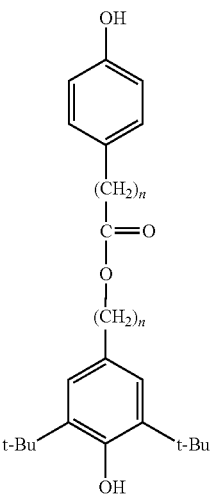

R = OH, COOH, COOAlkyl
n = 0,1,2,3...k

The following scheme shows the synthesis of 4-hydroxy phenyl acetic acid-3,5-di-tert butyl 4-hydroxybenzyl alcohol ester via the enzymatic route.

Scheme 4.
Synthesis of 4-hydroxy phenyl acetic
acid -3,5-di-tert butyl 4-hydroxybenzyl alcohol ester.

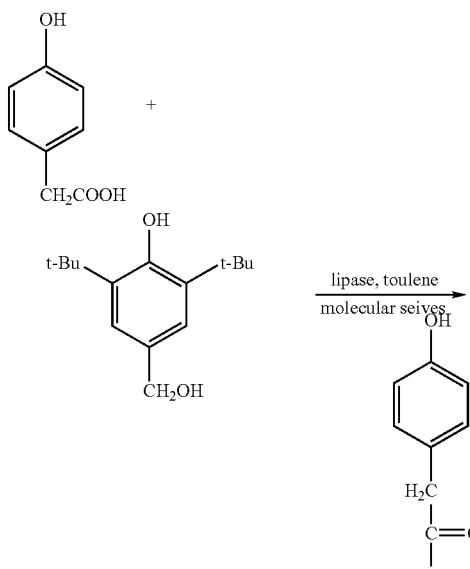

Compound 5

This procedure was also repeated in which toluene solvent was replaced by dimethoxy polyethylene glycol.

A transesterification approach is also possible via the enzymatic route as depicted in Scheme 5.

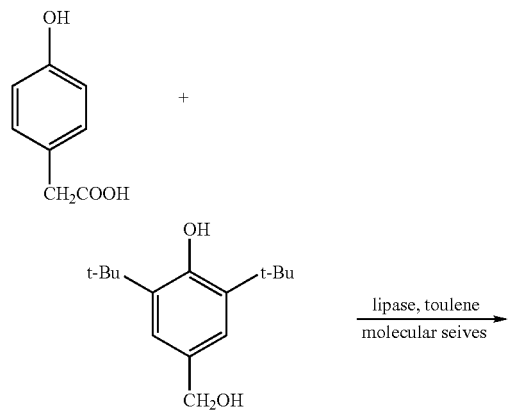

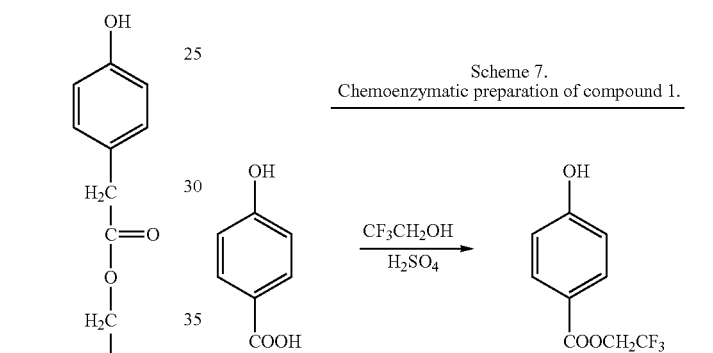

Compound 6 c) Chemoenzymatic Routes

Scheme 7 represents a chemoenzymatic route for the formation of macromonomer antioxidant compound 1.

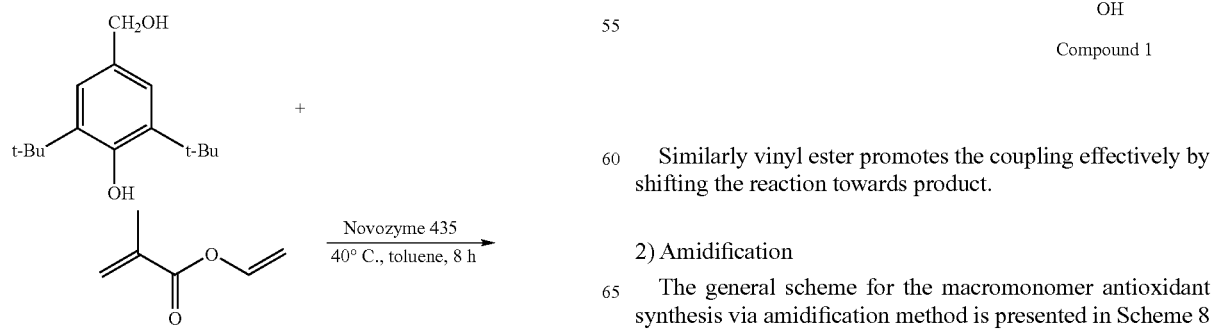

The macromonomer antioxidants of the present invention may also comprise an acrylate moiety as depicted in Scheme 6.

Similarly vinyl ester promotes the coupling effectively by shifting the reaction towards product.

2) Amidification

The general scheme for the macromonomer antioxidant synthesis via amidification method is presented in Scheme 8 for the chemical route and Scheme 9 for the enzymatic route.

Scheme 8.
Macromonomer antioxidant synthesis via chemical amidification.

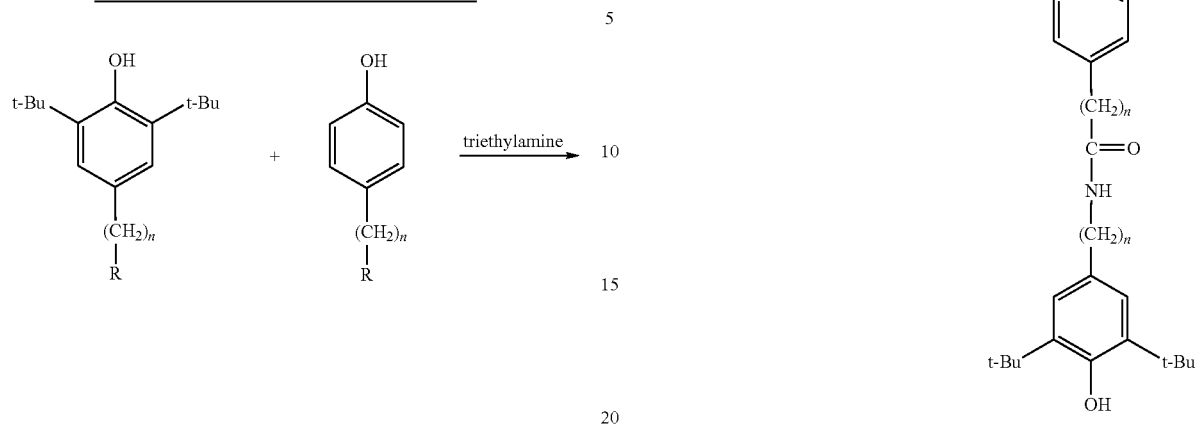

R = NH$_2$, COOH, COOalkyl
n = 0,1,2,3...k

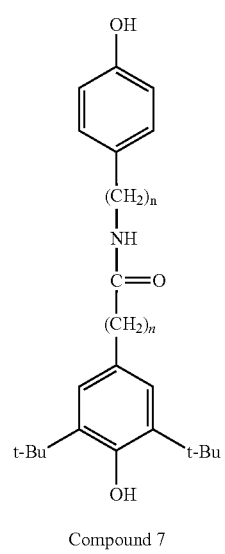

Compound 7

R = COCl, NH$_2$
n = 0,1,2,3...k

Scheme 8.
Macromonomer antioxidant synthesis via enzymatic amidification.

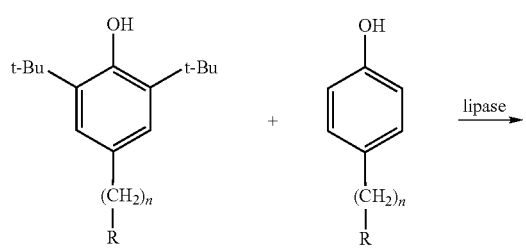

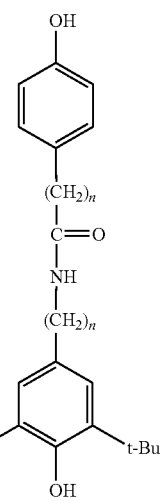

Compound 9

3) Ketone Formation

Under this synthetic route, Friedel-Craft acylation reactions are used to synthesize antioxidant macromonomers.

For example, 2,6-di-tert butyl phenol can be acylated with 4-hydroxy-benzoyl chloride in presence of Lewis acids like aluminum trichloride, boron trifluoride, or zinc chloride, etc. to produce Compound 10 as depicted in Scheme 10.

Scheme 10.
Friedel-Craft acylation.

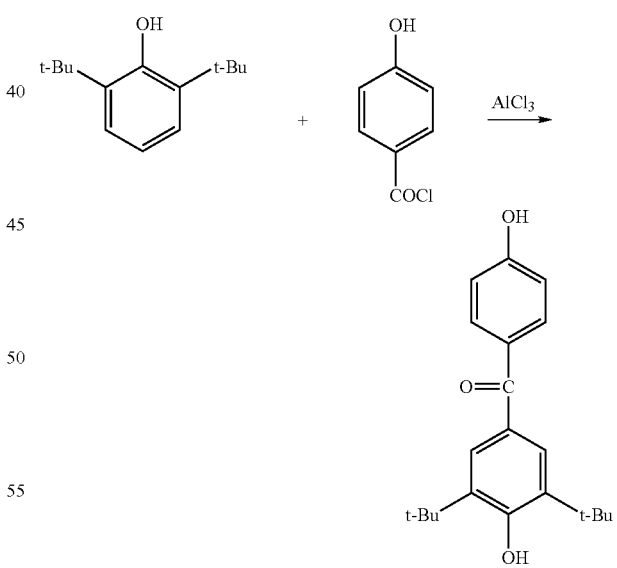

Compound 10

This reaction is equally applicable to 3,4 dihydroxy benzoyl chloride and 3,4,5 trihydroxy benzoyl chloride as acylating agents.

Resorcinol can be acylated with 3,5-di-tert-butyl-4-hydroxy-propionic acid, 3,5-di-tert-butyl-4-hydroxy acetic acid, or 3,5 di-tert-butyl-4-hydroxy-benzoic acid etc. in the presence of a Lewis acid like aluminum trichloride, boron trifluoride, zinc chloride etc. to form antioxidant macromonomers (Compound 11) as depicted in Scheme 11.

Scheme 11.
Acylation of resorcinol.

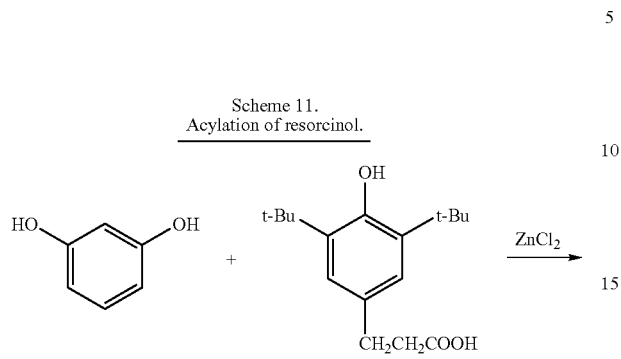

Compound 11

In a similar way, pyragallol can also be acylated with 3,5-di-tert-butyl-4-hydroxy-propionic acid, 3,5-di-tert-butyl-4-hydroxy acetic acid, or 3,5-di-tert-butyl-4-hydroxy-benzoic acid etc. in the presence of a Lewis acid like aluminum trichloride, boron trifluoride, zinc chloride, etc. to produce antioxidant monomers (Compound 12) as depicted in Scheme 12.

Scheme 12.
Acylation of pyragallol.

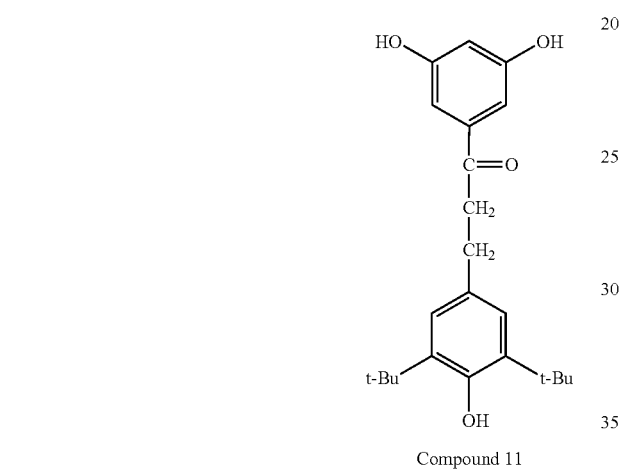

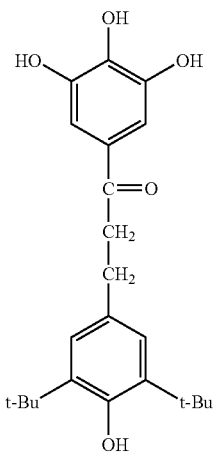

Compound 12

4) Alkylation

It is possible to reduce the carbonyl group in compounds 10, 11, and 12 to form a new set of macromonomer antioxidants shown below as compounds 13, 14, and 15, respectively, using a wide range of reducing agents including lithium aluminum hydride ($LiAlH_4$) and sodium borohydride ($NaBH_4$).

Compound 13

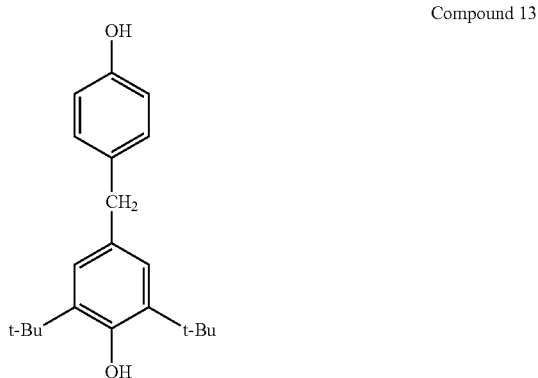

Compound 14

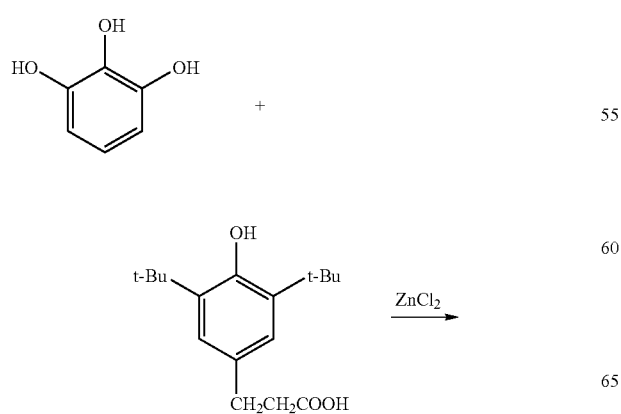

-continued

Compound 15

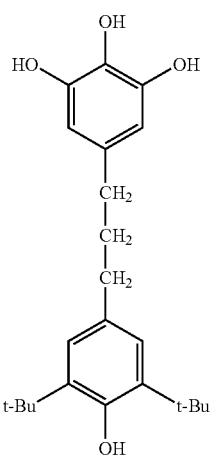

5) Anhydride Formation

The general scheme for this process is shown in Scheme 13 using triethylamine as a base in the formation of anhydride macromonomer structures.

Scheme 13.
Anhydride synthesis route macromonomer antioxidants.

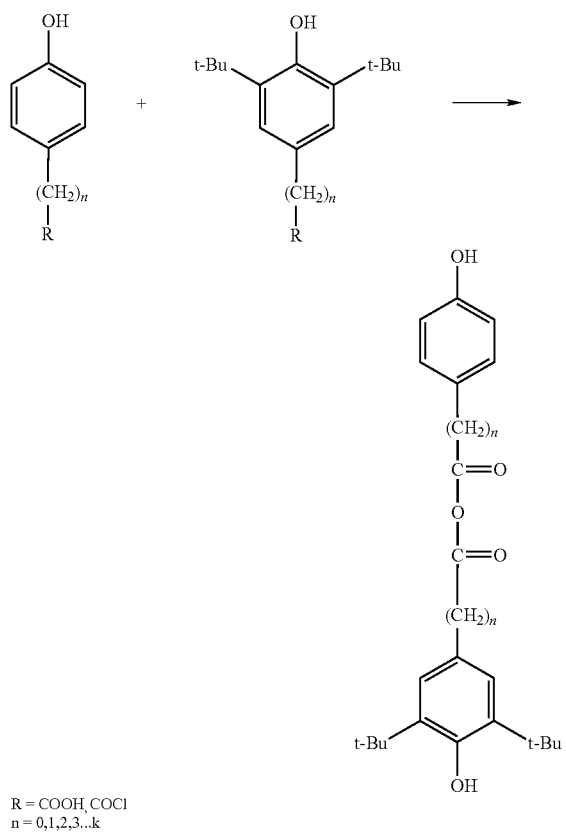

R = COOH, COCl
n = 0,1,2,3...k

Antioxidant Macromonome Polymerization

Polymerization of antioxidant macromonomers described above were enzymatically synthesized using either 1) horse radish peroxidase (HRP) as a biocatalyst or biomimetic type catalysts like 2) Hematin or Fe-Salen.

1) Enzymatic Polymerization of Macromonomer Antioxidants Using HRP

The typical scheme for enzymatic polymerization is presented in Scheme 14.

Scheme 14.
HRP enzymatic polmerization of macromonomer antioxidants.

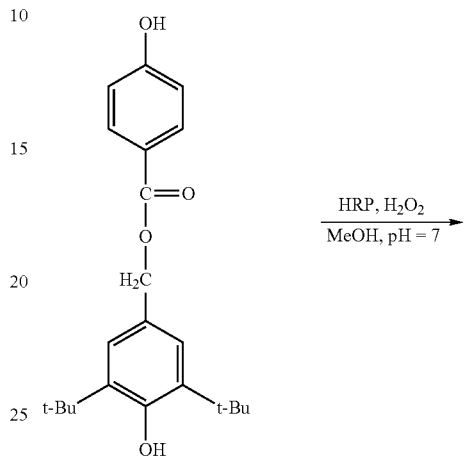

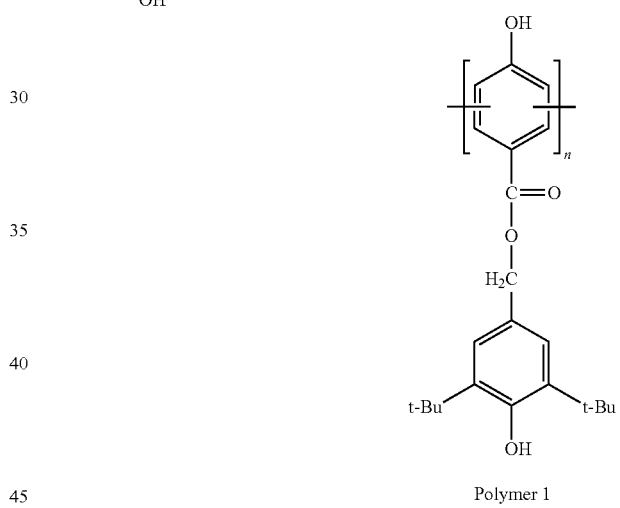

Polymer 1

In the case of macromonomers containing substituted hindered phenols, the enzymatically synthesized polymer chain may contain both C—C and C—O—C couplings in the backbone. There is a possibility that these polymeric materials may differ in color from that of starting monomeric antioxidants as a result of partial delocalization of electrons through C—C bonds between the phenolic repeating units. If the color of the polymeric antioxidant is due to its inherent nature arising from the C—C couplings and delocalization of electrons, it is possible to circumvent such color problem by using acrylate functionalized phenolic macromonomers in the formation of polymeric antioxidants.

Figure 2A:
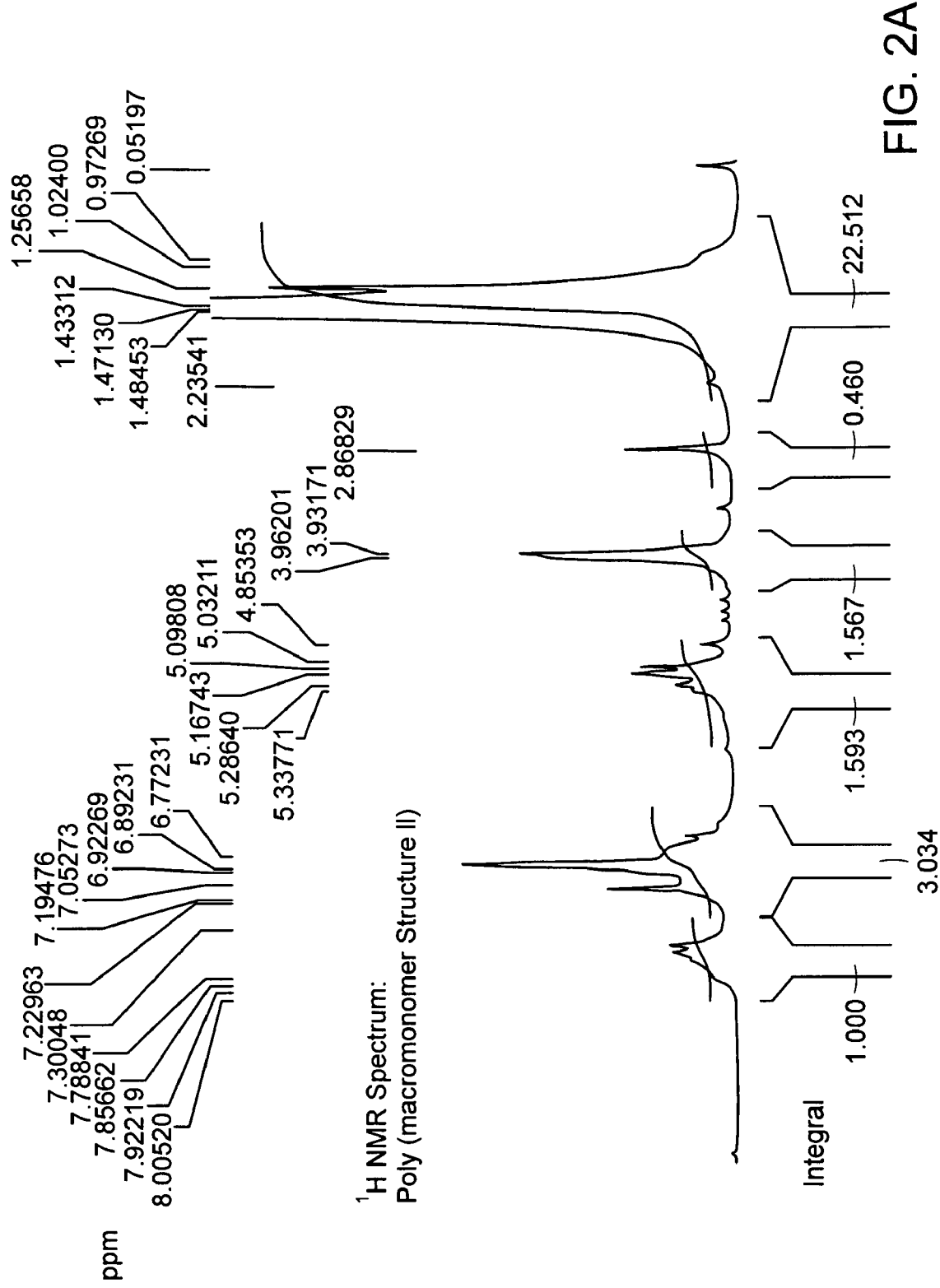
FIG. 2 depicts a) the $^1$H NMR spectrum of poly(macromonomer compound 1) formed from deacetylation of acetylated monomer (compound 1) and b) the $^1$H NMR spectrum of poly(macromonomer compound 6).
Figure 2B:
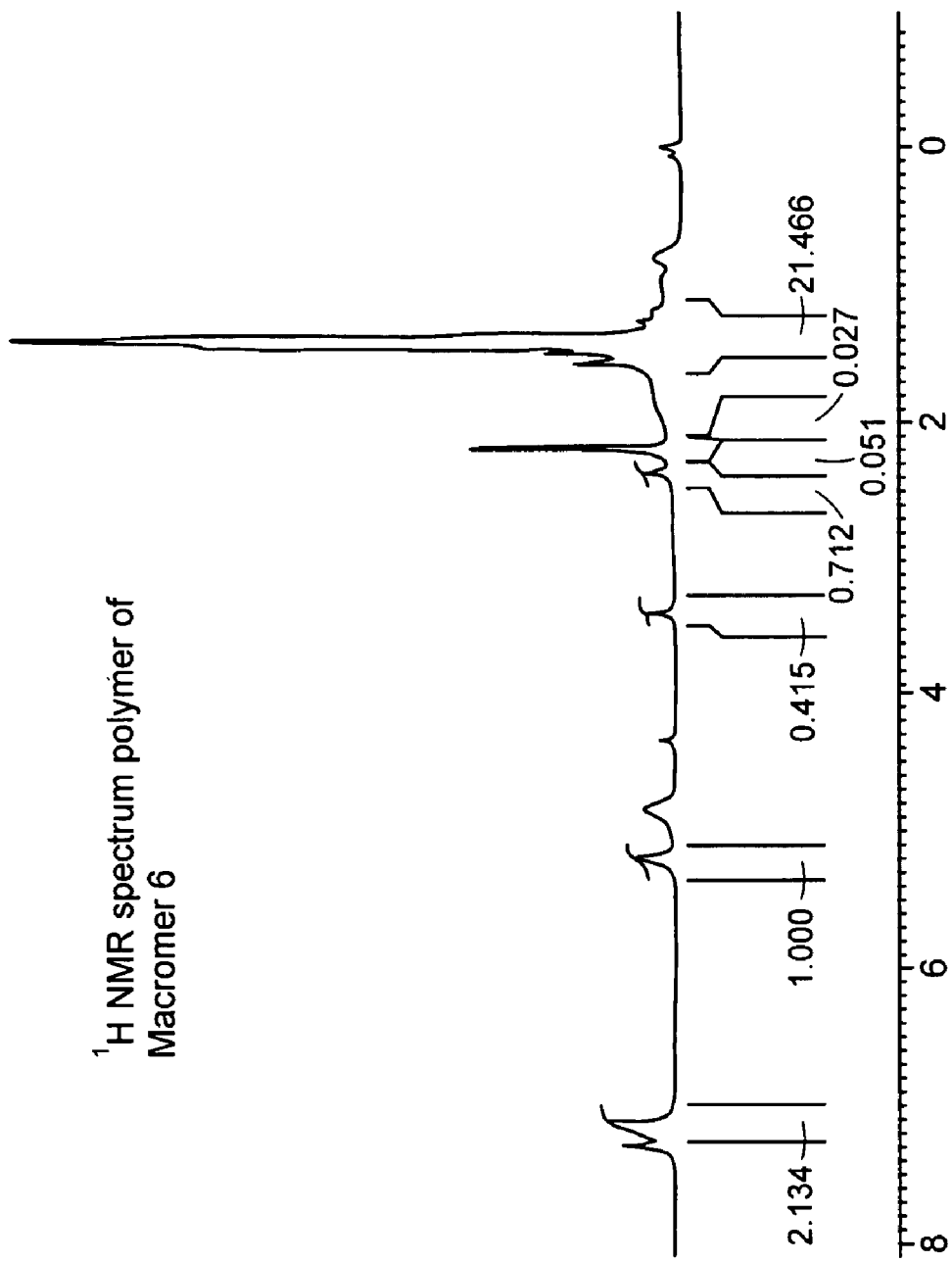

Macromonomer antioxidant compound 6 was polymerized using an initiator, α,α'-azobis(isobutyronitrile) (AUBN) to obtain polymeric macromonomer antioxidants. Polymerization reaction was performed in THF solution. The structure of the polymer was confirmed by high resolution NMR (FIG. 2b). The disappearance of the signals corresponding to olefinic protons indicated the polymerization reaction.

2) Biomimetic Polymerization of Macromonomer Antioxidants Using Fe-Salen

The typical scheme for biomimetic polymerization is presented in Scheme 15.

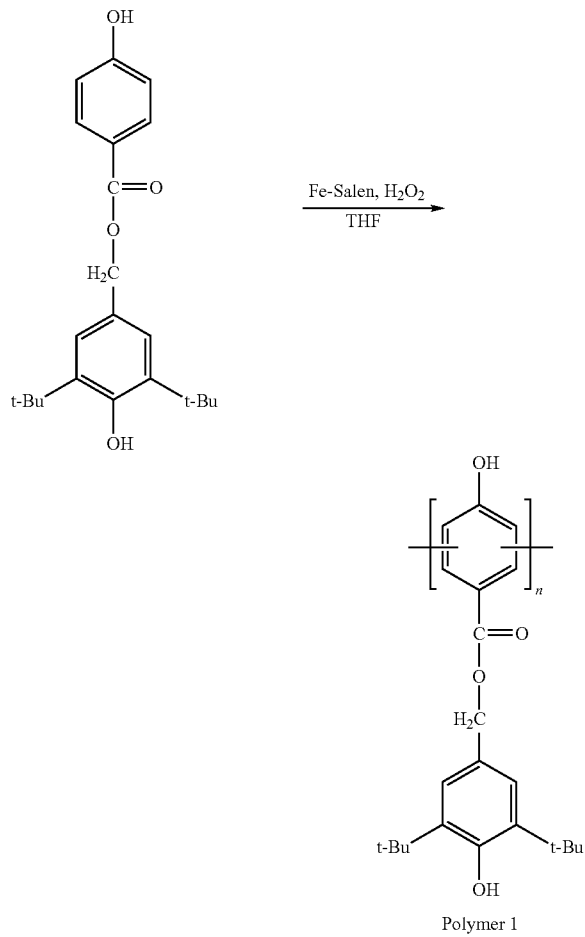

Performance of Polymeric Macromonomer Antioxidants in Polyolefins

The ASTM D3895 method was used to evaluate the performance of antioxidants in polyolefins. This is an accelerated ageing test at elevated temperatures under oxygen atmosphere. In the ASTM D3895 and DIN EN 728 method, a differential scanning calorimetry (DSC) instrument is used to detect the degradation by exothermic behavior of the polymeric materials containing antioxidants. The typical experimental conditions were as follows: the sample was heated at 20° C./min to reach 200° C. in the nitrogen atmosphere. At this temperature, the sample was held at constant 200° C. for 3 minutes in nitrogen atmosphere. At the end of this 3 minutes period, gas was changed to oxygen (20 ml/min flow rate). The sample was continued to hold at 200° C. till the sample starts degrading. This is indicated by sudden increase in the exothermic heat flow as presented in the DSC curve (See FIG. 3).

Figure 3:
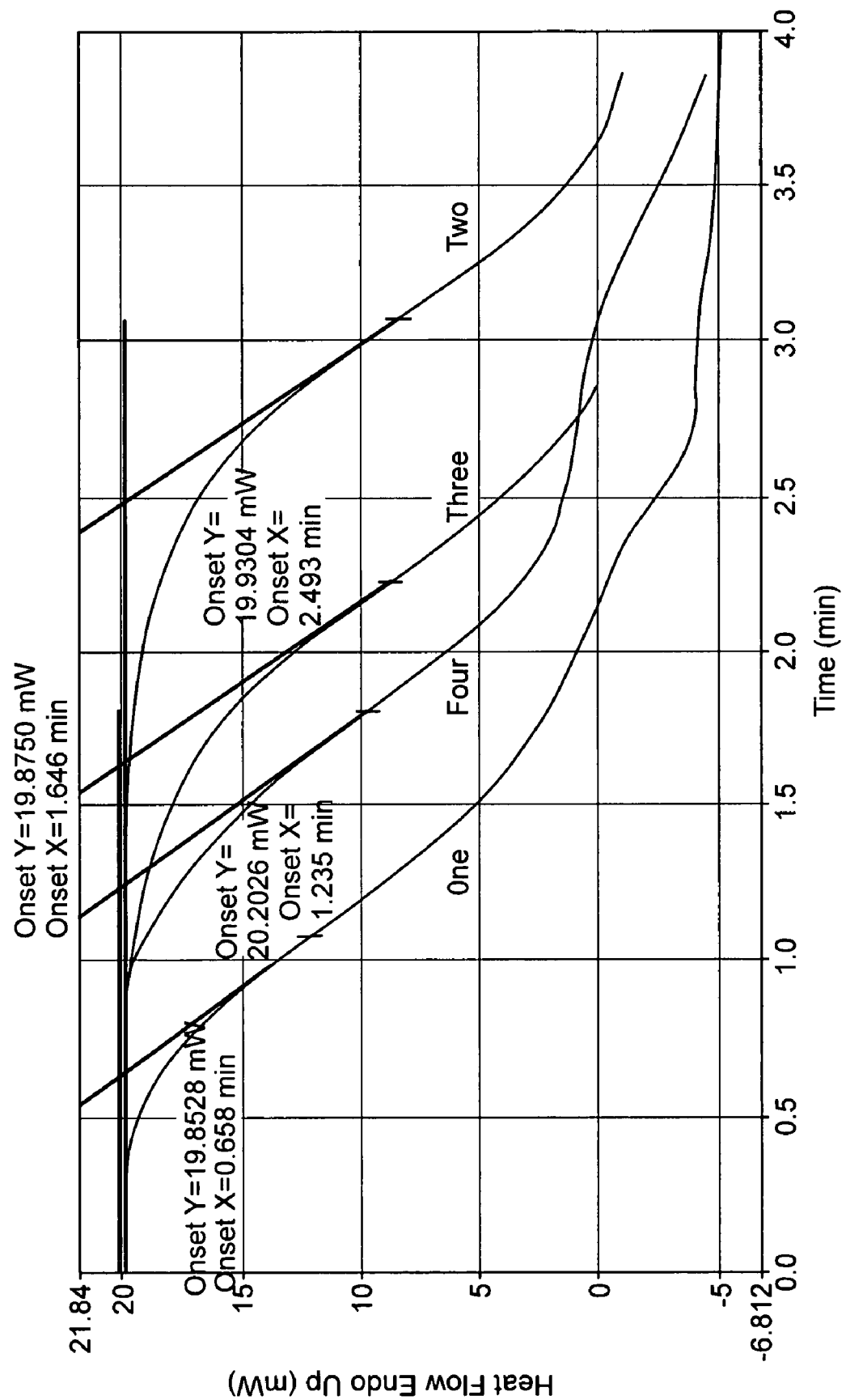
FIG. 3 depicts the comparison of oxidative induction time (OIT) (min) of polypropylene samples containing 200 ppm of polymeric macromonomer antioxidant (polymer 1) (trace two) and Irganox 1010 (trace one).

The isothermal oxidative induction time (OIT) is used to compare the performance polymeric antioxidants in polyolefins. The polypropylene samples were extruded into small pellets by mixing with 200 ppm by weight of antioxidants. FIG. 3 shows the OIT plots for these materials. The performance of polymeric macromonomer antioxidant is ca. 385% better compared to Irgonox 1010.

The performances of these antioxidants were also tested by comparing OIT values for polypropylene samples containing 0.5% level of antioxidants. The OIT values for PP containing polymeric macromonomer antioxidant and Irganox 1010 are 8.0 min and 33.2 minutes, respectively. These results are summarized in Table 1.

TABLE 1

Comparison of polymeric macromonomer antioxidants with monomeric antioxidants (ASTM D3895 method).

| Concentration of Antioxidant | OIT in Minutes for Polypropylene Samples with | |
|---|---|---|
| | Irganox | Polymer AO |
| 200 ppm | 0.7 min | 2.5 min |
| 5,000 ppm | 8.0 min | 33.0 min |

Physical Properties of the Polymeric Macromonomer Antioxidants

In certain embodiments, the polymeric macromonomer antioxidant of the subject compositions, e.g., which include repetitive elements shown in any of the macromonomer formulas, have molecular weights ranging from about 2000 or less to about 1,000,000 or more daltons, or alternatively about 10,000, 20,000, 30,000, 40,000, or 50,000 daltons, more particularly at least about 100,000 daltons, and even more specifically at least about 250,000 daltons or even at least 500,000 daltons. Number-average molecular weight (Mn) may also vary widely, but generally fall in the range of about 1,000 to about 200,000 daltons, or even from about 1,000 to about 100,000 daltons or even from about 1,000 to about 50,000 daltons. In one embodiment, Mn varies between about 8,000 and 45,000 daltons. Within a given sample of a subject polymer, a wide range of molecular weights may be present. For example, molecules within the sample may have molecular weights which differ by a factor of 2, 5, 10, 20, 50, 100, or more, or which differ from the average molecular weight by a factor of 2, 5, 10, 20, 50, 100, or more. For food or edible products (e.g., products fit for human consumption), the molecular weight is advantageously selected to be large enough so that an antioxidant polymer cannot be absorbed by the gastrointestinal tract, such as greater than 1000 amu. For antioxidant polymers blended with a polymeric material, the molecule weight is advantageously selected such that the rate of diffusion of the antioxidant polymer through the polymeric material is slow relative to the expected lifetime of the polymeric material.

One method to determine molecular weight is by gel permeation chromatography ("GPC"), e.g., mixed bed columns, $CH_2Cl_2$ solvent, light scattering detector, and off-line dn/dc. Other methods are known in the art.

In certain embodiments, the intrinsic viscosities of the polymers generally vary from about 0.01 to about 2.0 dL/g in chloroform at 40° C., alternatively from about 0.01 to about 1.0 dL/g and, occasionally, from about 0.01 to about 0.5 dL/g.

The glass transition temperature (Tg) of the subject polymers may vary widely, and depend on a variety of factors, such as the degree of branching in the polymer components, and the like. When the polymeric macromonomer antioxidant of the invention is a rigid solid, the Tg is often within the range of from about −10° C. to about 80° C., particularly between about 0 and 50° C. and, even more particularly between about 25° C. to about 35° C. In other embodiments, the Tg is low enough to keep the composition of the invention flowable at ambient temperatures. Then, the glass transition temperature of the polymeric macromonomer antioxidant used in the invention is usually about 0 to about 37° C., or alternatively from about 0 to about 25° C.

Antioxidant polymers of the present invention can be either homopolymers or copolymers. A copolymer preferably contains two or more or three or more different repeating monomer units, each of which has varying or identical antioxidant properties (including monomers having no antioxidant activity). The identity of the repeat units in a copolymer can be chosen to modify the antioxidant properties of the polymer as a whole, thereby giving a polymer with tunable properties. The second, third and/or further repeat units in a copolymer can be either a synthetic or natural antioxidant. In one example, a composition of the invention includes one or more homopolymers and one or more copolymers (e.g., in a blend). Preferably, both homopolymers and copolymers include two or more substituted benzene repeat units that are directly connected by a C—C or C—O—C bond. Preferably, at least 50%, such as at least 70%, for example, at least 80%, but preferably about 100% of the repeat units in a copolymer are substituted benzene repeat units directly connected by a C—C or C—O—C bond.

Antioxidant polymers of the present invention are typically insoluble in aqueous media. The solubility of the antioxidant polymers in non-aqueous media (e.g., oils) depends upon the molecular weight of the polymer, such that high molecular weight polymers are typically sparingly soluble in non-aqueous media. When an antioxidant polymer of the invention is insoluble in a particular medium or substrate, it is preferably well-mixed with that medium or substrate.

Antioxidant polymers of the present invention can be branched or linear, but are preferably linear.

Polymerization

Polymerization of the macromonomers can be catalyzed by a natural or synthetic enzyme or an enzyme mimetic capable of polymerizing a substituted benzene compound in the presence of hydrogen peroxide, where the enzyme or enzyme mimetic typically has a heme or related group at the active site. One general class of enzymes capable of catalyzing this reaction is commonly referred to as the peroxidases. Horseradish peroxidase, soybean peroxidase, *Coprinus cinereus* peroxidase, and *Arthromyces ramosus* peroxidase are readily available peroxidases. Other enzymes capable of catalyzing the reaction include laccase, tyrosinase, and lipase. Suitable enzymes are able to catalyze the formation of a carbon-carbon bond and/or a carbon-oxygen-carbon bond between two aryl (e.g., phenol) groups when a peroxide (e.g., hydrogen peroxide or an organic peroxide) is present. A subunit or other portion of a peroxidase is acceptable, provided that the active site of the enzyme is still functional.

Enzyme mimetics typically correspond to a part of an enzyme, so that they can carry out the same reaction as the parent enzyme but are generally smaller than the parent enzyme. Also, enzyme mimetics can be designed to be more robust than the parent enzyme, such as to be functional under a wider variety of conditions (e.g., different pH range and/or aqueous, partially aqueous and non-aqueous solvents) and are generally less subject to degradation or inactivation. Suitable enzyme mimetics include hematin, tyro sinase-model complexes and metal-salen (e.g., iron-salen) complexes. Hematin, in particular, can be functionalized to allow it to be soluble under a wider variety of conditions is disclosed in U.S. application Ser. No. 09/994,998, filed Nov. 27, 2001, the contents of which are incorporated herein by reference.

The enzymes and enzyme mimetics described above can be immobilized on a solid. In addition, the enzymes and enzyme mimetics can be dispersed in a solution or suspension.

The macromonomers described herein can also be polymerized by non-enzymatic chemical methods. For example, polymerization can be catalyzed by metal compounds such as iron chloride or a metallocene. Also, polymerization can be catalyzed by cationic, anionic or free radical initiators such as N,N-azobisisobutyromtrile (AIBN), acetylacetone and peroxides (e.g., tert-butyl hydroxide, benzyl peroxide). Polymerizations of the present invention can be carried out under a wide variety of conditions. The pH is often between about pH 1.0 and about pH 12.0, typically between about pH 6.0 and about pH 11.0. The temperature is generally above about 0° C., such as between about 0° C. and about 45° C. or between about 15° C. and about 30° C. (e.g., room temperature). The solvent can be aqueous (preferably buffered), organic, or a combination thereof. Organic solvents are typically polar solvents such as ethanol, methanol, isopropanol, dimethylformamide (DMF), dioxane, acetonitrile, dimethylsulfoxide (DMSO) and tetrahydrofuran (THF). The concentration of macromonomer or comacromonomers is typically 0.001 M or greater. Also, the concentration of buffer is typically 0.001 M or greater.

Preferably, the enzyme or enzyme mimetic is added to the solution after addition of the antioxidant macromonomer or comacromonomers. A peroxide is then added incrementally to the reaction mixture, such as not to de-activate the enzyme or enzyme mimetic, until an amount approximately stoichiometric with the amount of antioxidant macromonomer or comacromonomer has been added.

Although the enzyme or enzyme mimetic or the chemical initiator is responsible for formation of phenol-based free radicals needed for chain propagation, the coupling of radicals to form a polymer chain is controlled by the phenoxy radical and solvent chemistries. Further details regarding the coupling of phenoxy radicals can be found in "Enzymatic catalysis in monophasic organic solvents," Dordick, J. S., *Enzyme Microb. Technol.* 11:194-211 (1989), the contents of which are incorporated herein by reference. Coupling between substituted benzene monomers typically occurs ortho and/or para to a hydroxyl group. Coupling rarely occurs meta to a hydroxyl group.

Polymerization preferably results in the formation of C—C bonds between substituted benzene repeat units (i.e., the benzene rings are directly attached to each other in a chain). Preferred polymers will contain at least about 99% C—C bonds, at least about 98% C—C bonds, at least about 95% C—C bonds, at least about 90% C—C bonds, at least about 80% C—C bonds, at least about 70% C—C bonds, at least about 60% C—C bonds or at least about 50% C—C bonds. Especially preferred polymers contain about 100% C—C bonds.

Applications

The antioxidant polymers of the present invention can be used in a variety of applications. Antioxidant polymers of the present invention can be present in a wide variety of compositions where free radical mediated oxidation leads to deterioration of the quality of the composition, including edible products such as oils, foods (e.g., meat products, dairy products, cereals, beverages, crackers, potato flakes, bakery products and mixes, dessert mixes, nuts, candies, etc.), and other products containing fats or other compounds subject to oxidation (e.g., chewing gum, flavorings, yeast, etc.).

Antioxidant polymers can also be present in plastics and other polymers, elastomers (e.g., natural or synthetic rubber), petroleum products (e.g., mineral oil, fossil fuels such as gasoline, kerosene, diesel oil, heating oil, propane, jet fuel), adhesives, lubricants, paints, pigments or other colored items, soaps and cosmetics (e.g., creams, lotions, hair products). Soaps and cosmetics, in particular, benefit from the addition of a large proportion of one or more antioxidant polymers of the invention. Soaps and cosmetics can contain, for example, about 1% to about 20% (e.g., about 5% to about 15%) by weight of antioxidant polymer.

The antioxidant polymers can be used to coat a metal as a rust and corrosion inhibitor.

Antioxidant polymers additionally can protect antioxidant vitamins (Vitamin A, Vitamin C, Vitamin E) and pharmaceutical products (i.e., those containing a pharmaceutically active agent) from degradation. The addition of antioxidant polymers is particularly advantageous when the vitamin or pharmaceutically active agent is present in a liquid composition, although the antioxidant polymers is expected also to have a benefit in solid compositions.

In food products, the antioxidant polymers will prevent rancidity. In plastics, the antioxidant polymers will prevent the plastic from becoming brittle and cracking.

Antioxidant polymers of the present invention can be added to oils to prolong their shelf life and properties. These oils can be formulated as vegetable shortening or margarine. Oils generally come from plant sources and include cottonseed oil, linseed oil, olive oil, palm oil, corn oil, peanut oil, soybean oil, castor oil, coconut oil, safflower oil, sunflower oil, canola (rapeseed) oil and sesame oil. These oils contain one or more unsaturated fatty acids such as caproleic acid, palmitoleic acid, oleic acid, vaccenic acid, elaidic acid, brassidic acid, erucic acid, nervomc acid, linoleic acid, eleosteric acid, alpha-linolenic acid, gamma-linolenic acid, and arachidonic acid, or partially hydrogenated or trans-hydrogenated variants thereof. Antioxidant polymers of the present invention are also advantageously added to food or other consumable products containing one or more of these fatty acids.

The shelf life of many materials and substances contained within the materials, such as packaging materials, are enhanced by the presence of an antioxidant polymer of the present invention. The addition of an antioxidant polymer to a packaging material is believed to provide additional protection to the product contained inside the package. In addition, the properties of many packaging materials themselves, particularly polymers, are enhanced by the presence of an antioxidant regardless of the application (i.e., not limited to use in packaging). Common examples of packaging materials include paper, cardboard and various plastics and polymers. A packaging material can be coated with an antioxidant polymer (e.g., by spraying the antioxidant polymer or by applying as a thin film coating), blended with or mixed with an antioxidant polymer (particularly for polymers), or otherwise have an antioxidant polymer present within it. In one example, a thermoplastic polymer such as polyethylene, polypropylene or polystyrene is melted in the presence of an antioxidant polymer in order to minimize its degradation during the polymer processing. An antioxidant polymer can also be co-extruded with a polymeric material.

One example of a packaging material included in the present invention is commonly referred to as "smart packaging". Smart packaging is designed, for example, such that it controls gas exchange through the packaging. Examples of smart packaging are described in U.S. Pat. Nos. 5,911,937, 5,320,889 and 4,977,004, the contents of which are incorporated herein in their entirety. One conventional type of smart packaging involves a layer of an oxygen barrier such as nylon or poly(ethylene-co-vinyl alcohol) that is typically sandwiched between one or more layers of a moisture-resistant polymer or polymer blend such as polyethylene terephthalate, poly(vinylidene chloride), poly(vinyl chloride), poly (ethylene) or poly(propylene). The layers of moisture-resistant polymer can be either the same or different. In the present invention, one or more of the antioxidant polymers described herein can be added as an additional layer or can be blended with a layer of the packaging material.

One example of a composition that is particularly suitable as a packaging material includes polyethylene and polymer 1, typically where the two polymers are blended together. The proportion of polymer 1 in the composition is typically about 1 ppm to about 1,000 ppm, such as about 10 ppm to about 100 ppm. The composition can be, for example, in the form of a film or a pellet. The composition can also include a macromonomeric antioxidant, such as compounds 1-15. When the macromonomeric antioxidant is present, the concentration is typically about 1 ppm to about 1,000 ppm.

The concept of having a mixture of an antioxidant polymer and another antioxidant or polymer can generally be applied to combinations of one or more antioxidant polymers described herein and one or more synthetic and/or natural monomeric and/or oligomeric antioxidants and/or preservatives. Such compositions are expected to have both short-term and long-term antioxidant activity. The ratio of polymer to macromonomer and/or oligomer in a composition can be selected so that the composition has the desired set of properties. For example, the ratio of polymer to macromonomer and/or oligomer can be about 1:100 to about 100:1, such as about 1:10 to about 10:1. Typically, the absolute concentration of antioxidant polymers in such compositions ranges from about 0.1 ppm to about 10,000 ppm.

EXEMPLIFICATION

Example 1

Chemical coupling of acid chloride and antioxidant-alcohol. Thionyl chloride was added drop wise to the suspension of 4-acetoxy benzoic acid in chloroform and the reaction mixture was refluxed. After refluxing the reaction mixture for 4 hours; chloroform and excess thionyl chloride were distilled out under vacuum. The white colored acid chloride product was dried under vacuum for 2 hours and then dissolved in dry dichloromethane. The solution of triethylamine and 3,5 di-tert-butyl-4-hydroxy-benzyl alcohol in dry dichloromethane was added drop wise to it to obtain a yellow colored clear solution and the reaction mixture was stirred for additional 5 hours at room temperature in nitrogen atmosphere. The saturated aqueous sodium bicarbonate solution was then added and the reaction mixture was stirred for additional 30 minutes. The organic layer was separated and triethylamine-hydrochloride was washed off with water, and the product was dried and evaporated under vacuum and subjected later to column chromatography (ethyl acetate-petroleum ether) to obtain the desired ester.

The above ester product was then dissolved in 2% HCl-MeOH solution and stirred at room temperature for deacetylation to occur. After 5 hours, the reaction mixture was poured into large amount of ice-cold water and the solution was extracted with ethyl acetate, and the product was evaporated and then dried. The $^1$H NMR spectra of starting materials 4-acetoxy benzoic acid and 3,5-di-tert butyl 4-hydroxy benzyl alcohol and coupled product are depicted in FIGS. 1a-1c, respectively.

Example 2

Enzymatic synthesis of antioxidant macromonomer, 4-hydroxy phenyl acetic acid-3,5-di-tert butyl 4-hydroxybenzyl alcohol ester. To the suspension of 3,5 di-tert-butyl-4-hydroxy-benzyl alcohol and 4-hydroxy-phenyl-acetic acid in toluene in the presence of molecular sieves was added *Candida Antarctica* Lipase B (novozyme 435). The reaction mixture was stirred at 60° C. for 20 hours. After the completion of reaction; macromonomer (Compound 5) was purified using column chromatography (ethyl acetate petroleum ether). The molecular structure of this compound was confirmed to Structure VII by high resolution proton NMR.

Example 3

Enzymatic synthesis of antioxidant macromonomer, 4-hydroxy phenyl acetic acid-3,5-di-tert butyl 4-hydroxybenzyl alcohol ester involving transesterification. To the suspension of 3,5 di-tert-butyl-4-hydroxy-benzyl alcohol and 4-hydroxy-phenyl-acetic acid methyl ester in toluene was added *Candida Antarctica Lipase* B (novozyme 435). The molecular sieves were added to trap methanol that was produced as a result of transesterification. The reaction mixture was stirred at 60° C. for 20 hours. Macromonomer compound (Compound 5) was separated using column chromatography. The formation of the compound was confirmed by high resolution proton NMR.

Example 4

Acrylate based antioxidant vinyl macromonomers. Macromonomer antioxidant was prepared using lipase (Novozyme 435) to couple 3,5-di-tert-butyl-4-hydroxybenzyl alcohol to the vinyl ester monomer of methacrylic acid. The enzymatic reaction was carried out at 40° C. for 8 hours in toluene. The reaction product was separated and the structure of the macromonomer product was confirmed by high resolution proton NMR.

Example 5

Chemoenzymatic coupling. 4-hydroxy 2,2,2-trifluoro ethyl benzoate was synthesized by adding a trace amount of sulfuric acid to the mixture of trifluoro ethanol and 4-hydroxy-benzoic acid. Trifluoro-ester promotes the coupling effectively by shifting the reaction towards product the ester. The lipase catalyzed transesterification of this compound with 3,5 di-tert-butyl-4-hydroxy-benzyl alcohol gives the compound in Structure II (K. Faber, Biotransformations in Organic Synthesis, Springer, New York, 2000, page 347).

Example 6

HRP enzymatic polymerization of macromonomer antioxidant Macromonomer (compound 1, 0.5 mmole) was dissolved in MeOH: pH=7 (10 ml) phosphate buffer and 5 mg of HRP enzyme was added to it. To the reaction mixture 5% hydrogen peroxide solution was added incrementally over the period of 3 hours. After completion of addition, the reaction mixture was stirred for additional 24 hours. After completion of reaction methanol and water were removed, and the product was washed with water and dried. The polymer was characterized using high resolution proton NMR and the molecular weight was estimated to be 3500 using gel permeation chromatography (GPC) with reference polystyrene standards.

Example 7

Fe-salen biomimetic polymerization of macromonomer antioxidant. Compound 1 (4 g) was dissolved in THF (20 ml) and 80 mg of Fe-Salen was added to it. To the reaction mixture 25% hydrogen peroxide solution was added incrementally over the period of 1 hour. After completion of addition, the reaction mixture was stirred for additional 24 hours. After completion of reaction THF was removed, product washed with water and dried.

Incorporation by Reference

All of the patents and publications cited herein are hereby incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

I claim:

1. A compound represented by the following structural formula:

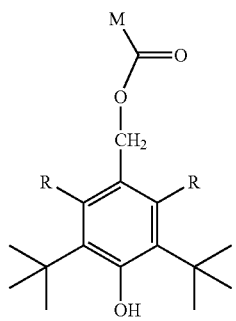

wherein, independently for each occurrence:

R is —H, $C_{1-6}$ alkyl, —OH, —NH$_2$, —SH, aryl, ester or

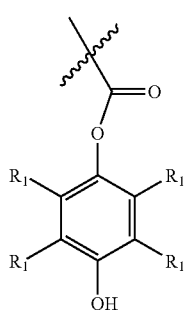

$R_1$ is —H, $C_{1-6}$alkyl, aryl, aralkyl, —OH, —NH$_2$, —SH or ester, wherein at least one $R_1$ adjacent to the —OH group is a bulky alkyl group;
M is:
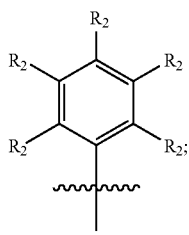
$R_2$ is —H, $C_{1-6}$ alkyl, —OH, —NH$_2$, —SH aryl, ester or
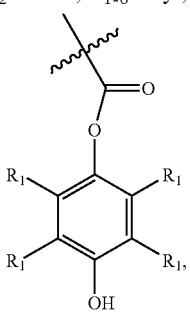
wherein $R_2$ in the para position is —OH;
wherein at least one $R_2$ adjacent to the para position is —OH.
2. The compound of claim 1, wherein the $R_2$ groups in both positions adjacent to the para position are —OH.
* * * * *